United States Patent [19]
Olson et al.

[11] Patent Number: 5,861,273
[45] Date of Patent: *Jan. 19, 1999

[54] CHROMOSOMAL EXPRESSION OF HETEROLOGOUS GENES IN BACTERIAL CELLS

[75] Inventors: Pamela S. Olson, Cupertino; Desmond Mascarenhas, Los Altos Hills, both of Calif.

[73] Assignee: Celtrix Phamraceuticals, Inc., Santa Clara, Calif.

[ * ] Notice: The term of this patent shall not extend beyond the expiration date of Pat. No. 5,470,727.

[21] Appl. No.: 482,182

[22] Filed: Jun. 7, 1995

Related U.S. Application Data

[63] Continuation-in-part of Ser. No. 170,588, Dec. 21, 1993, Pat. No. 5,470,727.

[51] Int. Cl.⁶ .............................. C12P 21/02; C12N 1/21; C12N 15/64; C12N 15/70
[52] U.S. Cl. .................. 435/69.1; 435/172.1; 435/172.3 435/320.1; 435/252.33; 536/23.1; 536/24.1; 935/27; 935/38; 935/42; 935/52; 935/72
[58] Field of Search .................... 435/69.1, 71.1, 435/172.1, 320.1, 252.3, 252.33, 172.3; 536/23.1, 24.1; 935/22, 27, 33, 38, 41, 42, 52, 72

[56] References Cited

U.S. PATENT DOCUMENTS

| | | | |
|---|---|---|---|
| 4,425,437 | 1/1984 | Riggs | 435/320.1 |
| 4,431,739 | 2/1984 | Riggs | 435/252.33 |
| 4,563,424 | 1/1986 | Riggs | 435/69.4 |
| 4,704,362 | 11/1987 | Itakura et al. | 435/252.3 |
| 4,959,316 | 9/1990 | Stanislas et al. | 435/172.3 |
| 5,196,318 | 3/1993 | Baldwin et al. | 435/69.1 |
| 5,470,727 | 11/1995 | Mascarenhas et al. | 435/172.3 |

FOREIGN PATENT DOCUMENTS

| | | |
|---|---|---|
| 0166628 | 1/1986 | European Pat. Off. . |
| 0284126 | 9/1988 | European Pat. Off. . |

OTHER PUBLICATIONS

Goeddel, ed., *Methods in Enzymology*, Academic Press, Inc., San Diego, vol. 185, (1990).
Dulbecco et al., eds., *Virology* (1988) Lippincott Publishers, Philadelphia pp. 56–57.
Borck et al., "the construction in vitro of transducing derivatives of phage lambda" *Molec. Gen. Genet.* (1976) 149:199–207.
Struhl et al., "Functional genetic expression of eukaryotic DNA in *Escherichia coli*" *Proc. Natl. Acad. Sci. USA* (1976) 73:1471–1475.
Greener et al., "Identification of a novel genetic element in *Escherichia coli* K–12" *J. Bacteriol.* (1980) 144:312–321.
Russel et al., "Construction and characterization of glutaredoxin–negative mutants of *Escherichia coli*" *Proc, Natl. Acad. Sci. USA* (1988) 85:990–994.
Struhl et al, "Production of a functional eukaryotic enzyme in *Escherichia coli*: Cloning and expression of the yeast structural gene for imidazole–glycerolphoshate dehydratase (his3)" *Proc. Natl. Acad. Sci. USA* (1977) 74(12):5255–5259.
Diederich et al., "New cloning vectors for integration into the λ attachment site attB of the *Escherichia coli* chromosone" *Plasmid* (1992)28:14–24.

*Primary Examiner*—Mindy Fleisher
*Assistant Examiner*—Nancy J. Degen
*Attorney, Agent, or Firm*—Morrison & Foerster LLP

[57] ABSTRACT

The present invention provides compositions and methods for producing a heterologous protein of interest by inserting a copy of a gene encoding the heterologous protein of interest into the chromosome of a host cell, such as *E. coli*. A chromosomal transfer DNA (a circular, non-self-replicating DNA) is used to integrate the gene encoding the heterologous protein of interest into the host cell chromosome. The chromosomal transfer DNA comprises at least one selectable marker and may optionally include repeated DNA sequences flanking the selectable marker, facilitating chromosomal amplification of the integrated DNA. The gene encoding the protein of interest may be expressed after integration into the chromosome of the host cell; selection for chromosomal amplification may be performed prior to expression of the gene.

12 Claims, 26 Drawing Sheets pPC-21
PCR with primers
UBTGFβF 5'-GGGGCCGCGGTGGTGCTTTG
GATGCGGCCTATTGCTTTAGA-3'

UBTGFβR 5'-GGGGAATTCTTAGCTGCATT
TGCAAGACTTTACA-3'

FIG. 21

SEQUENCE LISTING ( 1 ) GENERAL INFORMATION:

( i i i ) NUMBER OF SEQUENCES: 81

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCCATCGATG CATTAAGCGG ATTTAGCCGG TTTCAG        3 6

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCCTGACTGC GTTAGCAATT TAACTGTGAT        3 0

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CTGGGCTGCT  TCCTAATGCA  GGAGTCGCAT                                    30
```

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
TAATACGACT  CACTATAGGG  AGA                                           23
```

( 2 ) INFORMATION FOR SEQ ID NO:5:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GATCTGTTGA  CAATTAATCA  TCGAACTAGT  TAACTAGTAC  GCAAGTT               47
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
TGCTAGTTAT  TGCTCAGCGG                                                20
```

( 2 ) INFORMATION FOR SEQ ID NO:7:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
CAGGATCCGA  TCGTGGAGGA  TGATTAAATG  GCGAAAGGGG  ACCCGCAC              48
```

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CAGGAAGCTT  ACGGCAGGAC  TTTAGCGGAA  AG                                32
```

(2) INFORMATION FOR SEQ ID NO:9:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:9:

GGGGCCGCGG TGGCATGCAG ATTTTCGTCA AGACTTTGA    39

(2) INFORMATION FOR SEQ ID NO:10:

(i) SEQUENCE CHARACTERISTICS:
(A) LENGTH: 116 base pairs
(B) TYPE: nucleic acid
(C) STRANDEDNESS: single
(D) TOPOLOGY: linear (xi) SEQUENCE DESCRIPTION: SEQ ID NO:10:

CAGATTTTCG TCAAGACTTT GACCGGTAAA ACCATAACAT TGGAAGTTGA ACCTTCCGAT    60

ACCATCGAGA ACGTTAAGGC GAAAATTCAA GACAAGGAAG GTATCCCTCC AGATCA    116

(2) INFORMATION FOR SEQ ID NO:11:

(i) SEQUENCE CHARACTERISTICS:
(A) LENGTH: 104 base pairs
(B) TYPE: nucleic acid
(C) STRANDEDNESS: single
(D) TOPOLOGY: linear (xi) SEQUENCE DESCRIPTION: SEQ ID NO:11:

ACAAAGATTG ATCTTTGCCG GCAAGCAGCT AGAAGACGGT AGAACGCTGT CTGATTACAA    60

CATTCAGAAG GAGTCCACCT TACATCTTGT GCTAAGGCTC CGCG    104

(2) INFORMATION FOR SEQ ID NO:12:

(i) SEQUENCE CHARACTERISTICS:
(A) LENGTH: 108 base pairs
(B) TYPE: nucleic acid
(C) STRANDEDNESS: single
(D) TOPOLOGY: linear (xi) SEQUENCE DESCRIPTION: SEQ ID NO:12:

ATACCTTCCT TGTCTTGAAT TTTCGCCTTA ACGTTCTCGA TGGTATCGGA AGGTTCAACT    60

TCCAATGTTA TGGTTTTACC GGTCAAAGTC TTGACGAAAA TCTGCATG    108

(2) INFORMATION FOR SEQ ID NO:13:

(i) SEQUENCE CHARACTERISTICS:
(A) LENGTH: 120 base pairs
(B) TYPE: nucleic acid
(C) STRANDEDNESS: single
(D) TOPOLOGY: linear (xi) SEQUENCE DESCRIPTION: SEQ ID NO:13:

GATCCGCGGA GCCTTAGCAC AAGATGTAAG GTGGACTCCT TCTGAATGTT GTAATCAGAC    60

AGCGTTCTAC CGTCTTCTAG CTGCTTGCCG GCAAAGATCA ATCTTTGTTG ATCTGGAGGG    120

(2) INFORMATION FOR SEQ ID NO:14:

(i) SEQUENCE CHARACTERISTICS:
(A) LENGTH: 135 base pairs
(B) TYPE: nucleic acid
(C) STRANDEDNESS: single
(D) TOPOLOGY: linear ( x i ) SEQUENCE DESCRIPTION: SEQ ID NO:14:

GATCCCCGCG GTGGTGGTCC GGAAACCCTG TGCGGTGCTG AACTGGTTGA CGCTCTTCAG 60

TTCGTTTGCG GTGACCGTGG TTTCTACTTC AACAAACCGA CCGGTTACGG TTCCTCCTCC 120

CGTCGTGCTC CGCAG 135

( 2 ) INFORMATION FOR SEQ ID NO:15:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

ACCGGTATCG TTGACGAATG CTGCTTCCGG TCCTGCGACC TGCGTCGTCT GGAAATGTAC 60

TGCGCTCCGC TGAAACCGGC TAAATCCGCT TAATGCATCG ATCTCGAG 108

( 2 ) INFORMATION FOR SEQ ID NO:16:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

AGCACGACGG GAGGAGGAAC CGTAACCGGT CGGTTTGTTG AAGTAGAAAC CACGGTCACC 60

GCAAACGAAC TGAAGAGCGT CAACCAGTTC AGCACCGCAC AGGGTTTCCG GACCACCACC 120

GCGGG 125

( 2 ) INFORMATION FOR SEQ ID NO:17:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AATTCTCGAG ATCGATGCAT TAAGCGGATT TAGCCGGTTT CAGCGGAGCG CAGTACATTT 60

CCAGACGACG CAGGTCGCAG GACCGGAAGC AGCATTCGTC AACGATACCG GTCTGCGG 118

( 2 ) INFORMATION FOR SEQ ID NO:18:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AATTGTCGAC ATTAATACGA CTCACTATAG GGAGACCACA ACGGTTTCCC TGAATTGTCG 60

ACATTAATAC GACTCACTAT AGGGAGACCA CAACGGTTTC CCTG 104

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CCCATCGATG CATTAAGCGG ATTTAGCCGG TTTCAG    36

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

TGCTAGTTAT TGCTCAGCGG    20

( 2 ) INFORMATION FOR SEQ ID NO:21:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

AAGGGCTTCA TCATCGGTAA TAGACA    26

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GAGGTACCAG CGCGGTTTGA TCAG    24

( 2 ) INFORMATION FOR SEQ ID NO:23:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

CAGCGTTATC CGCAACCTCA CC    22

( 2 ) INFORMATION FOR SEQ ID NO:24:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AATTGTCGAC ATTAATACGA CTCACTATAG GGAGACCACA ACGGTTTCCC TGAATTGTCG    60

ACATTAATAC GACTCACTAT AGGGAGACCA CAACGGTTTC CCTG    104

( 2 ) INFORMATION FOR SEQ ID NO:25:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CCCATCGATG CATTAAGCGG ATTTAGCCGG TTTCAG                                    36

( 2 ) INFORMATION FOR SEQ ID NO:26:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CAGATTTTCG TCAAGACTTT GACCGGTAAA ACCATAACAT TGGAAGTTGA ACCTTCCGAT           60

ACCATCGAGA ACGTTAAGGC GAAAATTCAA GACAAGGAAG GTATCCCTCC AGATCA              116

( 2 ) INFORMATION FOR SEQ ID NO:27:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CGCCAGGGTT TTCCCAGTCA CGAC                                                 24

( 2 ) INFORMATION FOR SEQ ID NO:28:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

AGCTTGGTGC TTCTTCTGCT GGTCTTGGAC CAGTTGTTCG TTGTGAACCA TGTGATGCAC           60

GAGCTTTAGC TCAATGTGCT CCACCACCAG CTGTT                                     95

( 2 ) INFORMATION FOR SEQ ID NO:29:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

TGTGCTGAAT TAGTTCGAGA ACCAGGTTGT GGTTGTTGTT TAACTTGTGC TTTATCTGAA           60

GGTCAACCAT GTGGTATTTA TACTGAACGT TGCGG                                     95

( 2 ) INFORMATION FOR SEQ ID NO:30:

( i ) SEQUENCE CHARACTERISTICS:
        ( A ) LENGTH: 109 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

TAGTGGTTTG CGTTGTCAAC CAAGCCCAGA TGAAGCTAGG CCTTACAAG CATTATTAGA           60

TGGTCGAGGT CTGTGTGTTA ATGCGTCCGC TGTTTCTCGA TTGCGCGCG                     109

( 2 ) INFORMATION FOR SEQ ID NO:31:

( i ) SEQUENCE CHARACTERISTICS:
    ( A ) LENGTH: 97 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

```
TCGACGCGCG  CAATCGAGAA  ACAGCGGACG  CATTAACACA  CAGACCTCGA  CCATCTAATA    60
ATGCTTGTAA  AGGCCTAGCT  TCATCTGGGC  TTGGTTG                                97
```

( 2 ) INFORMATION FOR SEQ ID NO:32:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
ACAACGCAAA  CCACTACCGC  AACGTTCAGT  ATAAATACCA  CATGGTTGAC  CTTCAGATAA    60
AGCACAAGTT  AAACAACAAC  CACAACCTGG  TTCTC                                 95
```

( 2 ) INFORMATION FOR SEQ ID NO:33:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
GAACTAATTC  AGCACAAACA  GCTGGTGGTG  GAGCACATTG  AGCTAAAGCT  CGTGCATCAC    60
ATGGTTCACA  ACGAACAACT  GGTCCAAGAC  CAGCAGAAGA  AGCACC                   106
```

( 2 ) INFORMATION FOR SEQ ID NO:34:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
TCGACGTGAG  ATGGAGGATA  CCTTAAACCA  TTTAAAATTT  TTGAACGTTT  TATCCCCGCG    60
TGGCGTTCAT  ATCCCGAATT  GCGAT                                             85
```

( 2 ) INFORMATION FOR SEQ ID NO:35:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

```
AAAAAGGCT   TCTACAAAAA  GAAACAATGC  CGTCCGAGTA  AGGGTCGTAA  ACGAGGTTTT    60
TGTTGGTGCG  TTGACAAATA  CGGT                                              84
```

( 2 ) INFORMATION FOR SEQ ID NO:36:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

CAACCGTTGC CGGGTTATAC TACTAAAGGC AAAGAAGATG TTCATTGTTA TTCTATGCAA    60

TCTAAATAAT GCATCTCGAG    80

( 2 ) INFORMATION FOR SEQ ID NO:37:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

AATTCTCGAG ATGCATTATT TAGATTGCAT AGAATAACAA TGAACATCTT CTTTGCCTTT    60

AGTAGTATAA CCCGGC    76

( 2 ) INFORMATION FOR SEQ ID NO:38:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

AACGGTTGAC CGTATTTGTC AACGCACCAA CAAAAACCTC GTTTACGACC CTTACTCGGA    60

CGGCATTGTT TCTTTTTGTA GAAG    84

( 2 ) INFORMATION FOR SEQ ID NO:39:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

CCTTTTTTAT CGCAATTCGG GATATGAACG CCACGCGGGG ATAAAACGTT CAAAAATTTT    60

AAATGGTTTA AGGTATCCTC CATCTCACG    89

( 2 ) INFORMATION FOR SEQ ID NO:40:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CGCGCTTATT TATTACCTGC CCCACCGGCA CCGGGTAACG CCTCCGAAA    49

( 2 ) INFORMATION FOR SEQ ID NO:41:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GCGAAGAGGA TCGTTCTGCG GGTTCCGTTG AATCTCCAAG TGTGAGTTCT ACCCATCGAG    60

TTAGCGACCC GAAA    74

(2) INFORMATION FOR SEQ ID NO:42:

(i) SEQUENCE CHARACTERISTICS:
      (A) LENGTH: 71 base pairs
      (B) TYPE: nucleic acid
      (C) STRANDEDNESS: single
      (D) TOPOLOGY: linear (xi) SEQUENCE DESCRIPTION: SEQ ID NO:42:

TTTCATCCGT TGCACTCTAA AATCATTATT ATTAAAAAGG GTCACGCAAA GGATTCTCAA        60

CGTTATAAGG T        71

(2) INFORMATION FOR SEQ ID NO:43:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (xi) SEQUENCE DESCRIPTION: SEQ ID NO:43:

GGATTATGAA AGCCAATCTA CCGACACTCA AAATTTTAGT AGTGAAAGTA AACGTGAAAC        60

CGAGTACGGC CCGTG        75

(2) INFORMATION FOR SEQ ID NO:44:

(i) SEQUENCE CHARACTERISTICS:
      (A) LENGTH: 44 base pairs
      (B) TYPE: nucleic acid
      (C) STRANDEDNESS: single
      (D) TOPOLOGY: linear (xi) SEQUENCE DESCRIPTION: SEQ ID NO:44:

TCGACACGGG CCGTACTCGG TTTCACGTTT ACTTTCACTA CTAA        44

(2) INFORMATION FOR SEQ ID NO:45:

(i) SEQUENCE CHARACTERISTICS:
      (A) LENGTH: 73 base pairs
      (B) TYPE: nucleic acid
      (C) STRANDEDNESS: single
      (D) TOPOLOGY: linear (xi) SEQUENCE DESCRIPTION: SEQ ID NO:45:

AATTTTGAGT GTCGGTAGAT TGGCTTTCAT AATCCACCTT ATAACGTTGA GAATCCTTTG        60

CGTGACCCTT TTT        73

(2) INFORMATION FOR SEQ ID NO:46:

(i) SEQUENCE CHARACTERISTICS:
      (A) LENGTH: 77 base pairs
      (B) TYPE: nucleic acid
      (C) STRANDEDNESS: single
      (D) TOPOLOGY: linear (xi) SEQUENCE DESCRIPTION: SEQ ID NO:46:

AATAATAATG ATTTAGAGT GCAACGGATG AAATTTCGGG TCGCTAACTC GATGGGTAGA        60

ACTCACACTT GGAGATT        77

(2) INFORMATION FOR SEQ ID NO:47:

(i) SEQUENCE CHARACTERISTICS:
      (A) LENGTH: 75 base pairs
      (B) TYPE: nucleic acid
      (C) STRANDEDNESS: single ( D ) TOPOLOGY: linear ( x i ) SEQUENCE DESCRIPTION: SEQ ID NO:47:

CAACGGAACC CGCAGAACGA TCCTCTTCGC TTTCGGAGGC GTTACCCGGT GCCGGTGGGG    60

CAGGTAATAA ATAAG    75

( 2 ) INFORMATION FOR SEQ ID NO:48:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GGTTGTTGTT TAACTTGTGC TTTATCTGAA GGTCAACCAT GTGGTATTTA TACTGAACGT    60

TGCGGTAGTG GTTTGCGTTG TCAACCAAGC CCAGATGAAG CTAGG    105

( 2 ) INFORMATION FOR SEQ ID NO:49:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

AGCGGATAAC AATTTCACAC AGGA    24

( 2 ) INFORMATION FOR SEQ ID NO:50:

( i ) SEQUENCE CHARACTERISTICS:
        ( A ) LENGTH: 103 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

TAAAGCACAA GTTAAACAAC AACCACAACC TGGTTCTCGA ACTAATTCAG CACAAACAGC    60

TGGTGGTGGA GCACATTGAG CTAAAGCTCG TGCATCACAT GGT    103

( 2 ) INFORMATION FOR SEQ ID NO:51:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

CGCCAGGGTT TTCCCAGTCA CGAC    24

( 2 ) INFORMATION FOR SEQ ID NO:52:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GACTGCAAGC TTCCGCGGTG GTGGTGCTTC TTCTGCTGGT CTTGGA    46

( 2 ) INFORMATION FOR SEQ ID NO:53:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:53:

CTCGATTGCG CGCTTATTTA TTACC 25

( 2 ) INFORMATION FOR SEQ ID NO:54:

( i ) SEQUENCE CHARACTERISTICS:
      ( A ) LENGTH: 52 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:54:

TCTCACGTCG ACACGGGCCG TACTCGGTTT CACGTTTACT CAGTACTAAA AT 52

( 2 ) INFORMATION FOR SEQ ID NO:55:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:55:

TGTTGGTGCG TCGACAAATA CGGTC 25

( 2 ) INFORMATION FOR SEQ ID NO:56:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:56:

AGCGGATAAC AATTTCACAC AGGA 24

( 2 ) INFORMATION FOR SEQ ID NO:57:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:57:

GACCGTATTT GTCGACGCAC CAACA 25

( 2 ) INFORMATION FOR SEQ ID NO:58:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:58:

CGCCAGGGTT TTCCCAGTCA CGAC 24

( 2 ) INFORMATION FOR SEQ ID NO:59:

( i ) SEQUENCE CHARACTERISTICS:
      ( A ) LENGTH: 23 base pairs ( B ) TYPE: nucleic acid
( C ) STRANDEDNESS: single
( D ) TOPOLOGY: linear ( x i ) SEQUENCE DESCRIPTION: SEQ ID NO:59:

TAATACGACT CACTATAGGG AGA 23

( 2 ) INFORMATION FOR SEQ ID NO:60:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:60:

GGGATATGAA CGCCACGCGG GGATAA 26

( 2 ) INFORMATION FOR SEQ ID NO:61:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:61:

GCGGAGAAAC CATAATTGCA TCTACTC 27

( 2 ) INFORMATION FOR SEQ ID NO:62:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:62:

CGTGAAACCG AGTACGGCCC GTGTC 25

( 2 ) INFORMATION FOR SEQ ID NO:63:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:63:

TGCTAGTTAT TGCTCAGCGG 20

( 2 ) INFORMATION FOR SEQ ID NO:64:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:64:

AAGGGCTTCA TCATCGGTAA TAGACA 26

( 2 ) INFORMATION FOR SEQ ID NO:65:

( i ) SEQUENCE CHARACTERISTICS:
( A ) LENGTH: 41 base pairs
( B ) TYPE: nucleic acid
( C ) STRANDEDNESS: single (D) TOPOLOGY: linear (xi) SEQUENCE DESCRIPTION: SEQ ID NO:65:

GGGGCCGCGG TGGTGCTTTG GATGCGGCCT ATTGCTTTAG A    41

(2) INFORMATION FOR SEQ ID NO:66:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:66:

GGGGAATTCT TAGCTGCATT TGCAAGACTT TACA    34

(2) INFORMATION FOR SEQ ID NO:67:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:67:

TAATACGACT CACTATAGGG AGA    23

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:68:

GGAAATGGAT ACACGAACCC    20

(2) INFORMATION FOR SEQ ID NO:69:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:69:

GCGGAGAAAC CATAATTGCA TCTACTC    27

(2) INFORMATION FOR SEQ ID NO:70:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:70:

GGGGGATCCG ATCGTGGAGG ATGATTAAAT GCACCACCAC CACCACCACG ACGACGACAA    60

AGCTTTGGAT GCGGCCTAT    79

(2) INFORMATION FOR SEQ ID NO:71:

(i) SEQUENCE CHARACTERISTICS:
        (A) LENGTH: 27 base pairs
        (B) TYPE: nucleic acid
        (C) STRANDEDNESS: single (D) TOPOLOGY: linear (xi) SEQUENCE DESCRIPTION: SEQ ID NO:71:

CCCGATTCTC TGGAAGTTCT GTTCCAA     27

(2) INFORMATION FOR SEQ ID NO:72:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:72:

TTGGAACAGA ACTTCCAGAG AATCGGGCAT G     31

(2) INFORMATION FOR SEQ ID NO:73:

(i) SEQUENCE CHARACTERISTICS:
    (A) LENGTH: 47 base pairs
    (B) TYPE: nucleic acid
    (C) STRANDEDNESS: single
    (D) TOPOLOGY: linear (xi) SEQUENCE DESCRIPTION: SEQ ID NO:73:

CTAGAACTTG CGTACTAGTT AACTAGTTCG ATGATTAATT GTCAACA     47

(2) INFORMATION FOR SEQ ID NO:74:

(i) SEQUENCE CHARACTERISTICS:
    (A) LENGTH: 220 base pairs
    (B) TYPE: nucleic acid
    (C) STRANDEDNESS: single
    (D) TOPOLOGY: linear (xi) SEQUENCE DESCRIPTION: SEQ ID NO:74:

CAGATTTTCG TCAAGACTTT GACCGGTAAA ACCATAACAT TGGAAGTTGA ACCTTCCGAT     60

ACCATCGAGA ACGTTAAGGC GAAAATTCAA GACAAGGAAG GTATCCCTCC AGATCAACAA     120

AGATTGATCT TTGCCGGCAA GCAGCTAGAA GACGGTAGAA CGCTGTCTGA TTACAACATT     180

CAGAAGGAGT CCACCTTACA TCTTGTGCTA AGGCTCCGCG     220

(2) INFORMATION FOR SEQ ID NO:75:

(i) SEQUENCE CHARACTERISTICS:
    (A) LENGTH: 243 base pairs
    (B) TYPE: nucleic acid
    (C) STRANDEDNESS: single
    (D) TOPOLOGY: linear (xi) SEQUENCE DESCRIPTION: SEQ ID NO:75:

GATCCCCGCG GTGGTGGTCC GGAAACCCTG TGCGGTGCTG AACTGGTTGA CGCTCTTCAG     60

TTCGTTTGCG GTGACCGTGG TTTCTACTTC AACAAACCGA CCGGTTACGG TTCCTCCTCC     120

CGTCGTGCTC CGCAGACCGG TATCGTTGAC GAATGCTGCT TCCGGTCCTG CGACCTGCGT     180

CGTCTGGAAA TGTACTGCGC TCCGCTGAAA CCGGCTAAAT CCGCTTAATG CATCGATCTC     240

GAG     243

(2) INFORMATION FOR SEQ ID NO:76:

(i) SEQUENCE CHARACTERISTICS:
    (A) LENGTH: 120 base pairs
    (B) TYPE: nucleic acid
    (C) STRANDEDNESS: single
    (D) TOPOLOGY: linear (xi) SEQUENCE DESCRIPTION: SEQ ID NO:76:

GGGAATTCAT GCATTATTTA GATTGCATAG AATAACAATG AACATCTTCT TTGCCTTTAG        60

TAGTATAACC CGGCAACGGT TGACCGTATT TGTCGACGCA CCAACAAAAA CCTCGTTTAC        120

(2) INFORMATION FOR SEQ ID NO:77:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:77:

GGAGGTGCAT GCCCGGGTCT GCCGGCCGTT CTTCTGCTGG TCTTGGACCA GTTG        54

(2) INFORMATION FOR SEQ ID NO:78:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:78:

CCCAGCACTC GTCCTGCTCT GACTACTATG        30

(2) INFORMATION FOR SEQ ID NO:79:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:79:

GTACGGGTCG TGAGCAGGAC GAGACTGATG ATAC        34

(2) INFORMATION FOR SEQ ID NO:80:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:80:

CCCGATTCTC TGGAAGTTCT GTTCCAA        27

(2) INFORMATION FOR SEQ ID NO:81:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:81:

GTAGGGCTAA GAGACCTTCA AGACAAGGTT        30

CHROMOSOMAL EXPRESSION OF HETEROLOGOUS GENES IN BACTERIAL CELLS

REFERENCE TO RELATED APPLICATIONS

This application is a continuation-in-part of U.S. patent application Ser. No. 08/170,588, filed on Dec. 21, 1993, now U.S. Pat. No. 5,470,727.

TECHNICAL FIELD

This invention is related to the field of expression of heterologous genes in bacteria.

BACKGROUND ART

Genetic engineering has made it possible to produce large amounts of heterologous proteins or polypeptides in bacterial cells by means of recombinant expression systems, especially by expression in such prokaryotes as *Escherichia coli* (*E. coli*).

The expressed heterologous proteins may be of mammalian, other eukaryotic, viral, bacterial, cyanobacterial, archaebacterial, or synthetic origin.

Unlike native bacterial proteins, which can often be efficiently accumulated within a bacterial cell even when encoded by a single chromosomal gene copy, there are no published reports to date of heterologous proteins being successfully accumulated within bacterial cells to levels exceeding 0.1% of total cell protein when expressed from a single chromosomal gene location.

0.1% of total cell protein (150 micrograms protein per trillion bacterial cells) is chosen as a practical measure of successful accumulation of protein because it approximately defines the lower limits of (a) economically significant accumulation of a desired protein by contemporary recombinant bacterial production standards, and (b) visual detection of a protein band by Coomassie-stained polyacrylamide gel analysis of whole bacterial cell extracts.

The relatively poor performance of non-bacterial genes when expressed in bacterial cells, even when placed under the control of the strongest known bacterial promoters, has been generally attributed to poor translation of the non-bacterial mRNAs and rapid degradation of newly synthesized non-bacterial proteins. It has almost universally been assumed that, in order to achieve successful accumulation of non-bacterial or heterologous proteins in bacterial cells, the genes encoding the heterologous proteins must be located on multicopy plasmid vectors.

A gene carried on one of the multicopy plasmids commonly used for cloning and expressing genes encoding heterologous proteins in *E. coli* usually has a copy number of more than 20 copies/cell. Even low copy number plasmids (e.g., pACYC177 and pLG339) generally exist at 6–10 copies per cell. One disadvantage imposed by plasmid gene dosages is that the expression of even minute amounts of some foreign proteins can kill host cells (see *Meth. Enzymol.* 185:63–65, ed. D. Goeddel, 1990). For this reason, it would be advantageous to reliably limit the copy number of genes encoding such toxic gene products, such as by integrating the gene into the bacterial chromosome at one or a small number of copies per cell. For example, such a system would allow one to make more representative cDNA expression libraries in bacterial hosts if the high-copy expression of one or more of the cDNAs in the library could kill the bacterial host or cause it to grow poorly.

Chromosomal integration of genes encoding heterologous polypeptides would also be advantageous as an alternative means for expression of heterologous proteins in bacterial host cells. Multicopy vectors are often unstable and require the use of antibiotics in the growth medium for maintenance. Present methods of integrating foreign genes into the bacterial chromosome suffer from inefficiency, the inability to control the site of integration of the foreign gene, and/or the inability to control the copy number of the integrated gene. Most importantly, all efforts to date to create recombinant DNA constructs on the bacterial chromosome, wherein a bacterial promoter is fused to a heterologous gene, have involved the creation of viral or plasmid intermediates carrying the construct. Because such intermediates replicate at high copy number, they may be difficult or even impossible to recover in cases where the foreign gene product is toxic to the bacterial cell. Expression of the encoded gene, even at low levels, may be toxic to the host cells, due to the high copy number of these intermediates, which effectively multiplies the level of expression.

Previous methods for achieving the integration of heterologous genes into the chromosome of a bacterial host include the use of phage lambda vectors. The phage DNA in circular form is inserted linearly into the bacterial chromosome by a single site specific recombination between a phage attachment site (attP), 240 bases long, and a bacterial attachment site (attB), only 25 bases long. The two sites have 15 bases in common. This site-specific recombination is catalyzed by a special integrase, specified by the phage gene INT (VIROLOGY pp. 56–57 (Lippincott, 2nd ed., R. Dulbecco and H. Ginsberg, eds., Philadelphia, Pa, 1985).

Phage vectors which are INT⁻ can be integrated into the chromosome in a normal fashion as long as integrase is supplied in trans, e.g., by an INT+ helper phage (see, e.g., Borck et al. (1976) *Molec. Gen. Genet.* 146:199–207).

Phage vectors which are both att– and INT– can likewise be integrated into the bacterial chromosome as double lysogens by using att+INT+ helper phage. Double lysogens are formed by linkage of the prophages at the bacterial attachment site and are integrated into the chromosome by general bacterial recombination between homologous sequences on the defective phage and on the helper phage (see e.g., Struhl et al. (1976) *Proc. Natl. Acad. Sci. USA* 73:1471–1475). Similarly, it is also possible to integrate non-replicating colE1 replicons into the genome of polA strains of *E. coli* by means of recombination between the host chromosome and homologous sequences carried by the plasmid vector (Greener and Hill (1980) *J. Bacteriol.* 144:312–321).

More recently, systems have been specifically designed for the integration of foreign genes into a bacterial host chromosome. For example, U.S. Pat. No. 5,395,763 (Weinberg et al.) discloses a chromosomal expression vector for the expression of heterologous genes. This vector was created utilizing a multicopy number plasmid intermediate, into which the gene of interest is cloned, placing the gene in operable linkage with the bacteriophage middle promoter, Pm. This plasmid intermediate, which comprises a defective Mu genome (lacking the genes necessary for the formation of phage particles) is introduced into a packaging strain to produce infectious Mu particles, which are then used to introduce the vector into host cells and integrate the vector into the host cell genome. This vector system is amplifiable once integrated into the host cell genome, but the mechanism of amplification (replicative transposition) is normally toxic to the host cell, due to integration of the replicating prophage into essential host cell genes (Neidhardt et al., ESCHERICHIA COLI AND Society for Microbiology, Neidhardt et al. eds., Washington, D.C., 1987). Because the amplification of this integrated prophage is normally toxic, it is very difficult to obtain and propagate a host cell strain carrying the amplified integrated DNA. This then requires that the gene be amplified each instance that protein production is desired.

Diederich et al. ((1992) "New plasmid vectors for integration into the 1 attachment site attB of the *Escherichia coli* chromosome", Plasmid 28:14–24) also disclose a system for introducing a gene onto the chromosome of a bacterial host cell. This system utilizes a set of multicopy plasmid vectors which can be integrated into a bacterial chromosome via a phage lambda attachment site. A DNA sequence encoding a promoter operably linked to a gene of interest is cloned into one of the described multicopy number plasmid vectors, the plasmid's origin of replication is removed by restriction enzymes, and the resulting DNA is recircularized and transferred to a host cell, where it integrates into the chromosome.

These new gene transfer systems suffer from the same defect as earlier systems. Both USP 5,395,763 (Weinberg et al.) and Diederich et al. require that the gene of interest be cloned into a multicopy number plasmid while in an operable configuration during the construction of the transfer DNA. The configuration of this multicopy number plasmid makes expression of toxic foreign genes difficult, if not impossible, because the (toxic) gene of interest will be expressed as the multicopy number plasmid is propagated.

Accordingly, there is a need for a method of producing heterologous proteins which can produce large amounts of protein and which minimizes any toxic effect of the heterologous protein to host cells during construction of the producing strain. Applicants have shown surprisingly high protein accumulation (approximately 20% of total cell protein) from expression of low (approximately two) copies of the gene encoding the heterologous protein as shown in Example 2.

SUMMARY OF THE INVENTION

The present invention provides methods and compositions for production of heterologous proteins in bacterial host cells such as *E. coli* by integrating a chromosomal transfer DNA (a circular, non-self replicating DNA) into the chromosome of a host cell. The chromosomal transfer DNA comprises one or more copies of a gene encoding the heterologqus protein of interest.

The present invention, therefore, provides a method for producing a heterologous protein of interest, comprising:

integrating a chromosomal transfer DNA into the chromosome of a host cell such that chromosomal amplification of the integrated DNA is facilitated, the chromosomal transfer DNA comprising at least one copy of a gene encoding a heterologous protein of interest and a selectable marker; and expressing the gene encoding the heterologous protein of interest, wherein the gene was at no time operably linked to a promoter functional in the host cell in a multicopy number plasmid during the construction of the transfer DNA, and wherein the heterologous protein of interest accumulates to a level of at least 0.1% of total cell protein.

The chromosomal transfer DNA may optionally comprise a promoter operably linked to the gene encoding the heterologous protein of interest, wherein the operable linkage is created by circularization of the chromosomal transfer DNA.

Optionally, the chromosomal transfer DNA may further comprise duplicate DNA flanking the selectable marker. The duplicate DNA may optionally comprise copies of the gene encoding the heterologous protein of interest operably linked to a promoter.

The methods for expression of heterologous proteins may optionally include the step of selecting for chromosomal amplification.

The invention also provides methods for producing a chromosomal transfer DNA, comprising ligating together fragments from a first and a second plasmid vector:

the first plasmid vector comprising a first origin of replication, and a first gene encoding a heterologous protein of interest wherein the first gene is not operably linked to a promoter;

the second plasmid vector comprising a second origin of replication, and a first promoter;

wherein the origins of replication and the promoter function in the host cell, and wherein either said first plasmid or said second plasmid comprises a selectable marker.

Optionally, the first plasmid may further comprise a second promoter not operably linked to the first gene encoding the heterologous protein of interest and the second plasmid may further comprise a second copy of the gene encoding the heterologous protein of interest not operably linked to the first promoter.

Also provided are chromosomal transfer DNAs for use in production of heterologous proteins of interest, comprising:

a non-bacterial gene of interest operably linked to a promoter functional in a host cell; and a selectable marker flanked by duplicate DNA, wherein said gene encoding a heterologous protein is at no time operably linked to a promoter functional in a host cell on a multicopy number plasmid vector during the construction of the transfer DNA.

Optionally, the chromosomal transfer DNA may further comprise two or more copies of the gene encoding the non-bacterial protein of interest, wherein the copies of the gene flank the selectable marker.

BRIEF DESCRIPTION OF THE DRAWINGS

FIG. 6 shows a chromosomal transfer DNA comprises a single copy of the gene encoding the heterologous protein of interest and two copies of a second gene which flank the selectable markers, facilitating chromosomal amplification after integration of the chromosomal transfer DNA. FIG. 7 shows the "double cassette" system utilized for expression of heterologous proteins in Examples 2 through 6 and Example 8. This embodiment of the chromosomal transfer DNA comprises two copies of the gene encoding the heterologous protein of interest flanking the selectable markers, facilitating chromosomal amplification of the integrated DNA. FIGS. 8 and 9 show alternate embodiments of "promoter-less" chromosomal transfer DNAs. These embodiments utilize a DNA sequence homologous to a segment of the host cell chromosome. Integration of promoter-less chromosomal transfer DNAs results in formation of an operably linkage between a host cell promoter and the gene encoding the heterologous protein of interest and the creation of duplicate DNA sequences flanking the selectable markers.

FIG. 21 shows the strategy used to construct the chromosomal transfer DNA used to integrate and express the gene encoding a DsbA::ubiquitin::TGF-β2 fusion protein.

MODES FOR CARRYING OUT THE INVENTION

Figure 1:
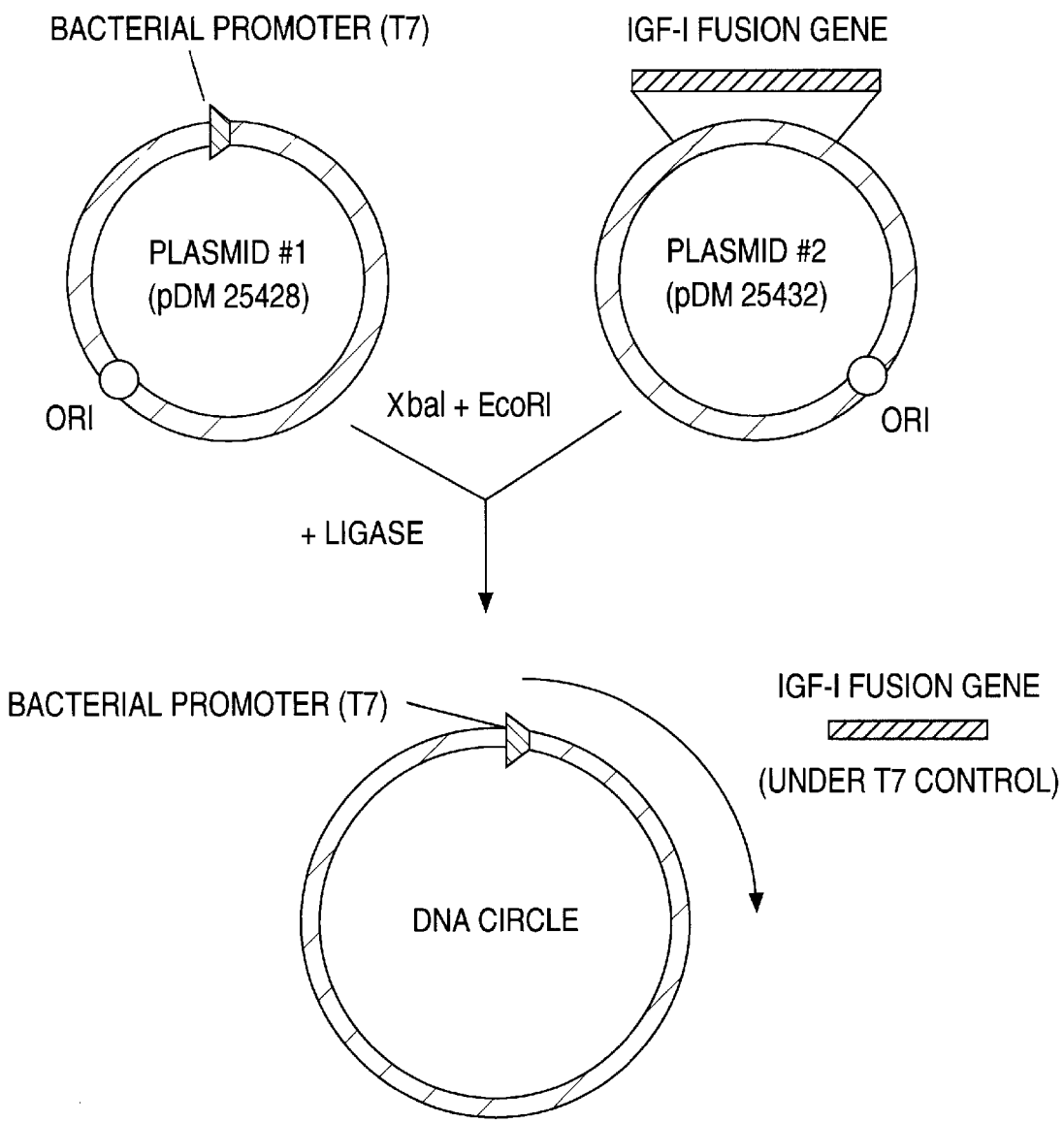
FIG. 1 shows steps in the in vitro formation of a chromosomal transfer DNA, a DNA circle which lacks an origin of replication (and thus is incapable of self-replication) and is suitable for integration of a foreign gene into the bacterial chromosome. Until the chromosomal transfer DNA is formed, the foreign gene to be expressed (here an IGF-I fusion gene) is separated from a functional bacterial promoter (here the T7 promoter).

The present invention resides in (a) the creation of an operable linkage between a promoter and a gene encoding a heterologous protein of interest with the linkage being formed either during the construction of a chromosomal transfer DNA or as a result of its integration into the host cell chromosome and (b) the simultaneous creation of a means for the appropriate chromosomal amplification of the integrated gene of interest.

In the preferred embodiments, the creation of the chromosomal transfer DNA simultaneously achieves two goals;

(1) the operable linkage of the promoter and the gene of interest and (2) the positioning of duplicate DNA sequences flanking a selectable marker (which can function as a means to facilitate the amplification of the chromosomal transfer DNA). Another embodiment creates the operable linkage between the gene and the promoter during creation of the chromosomal transfer DNA, while the means for chromosomal amplification (duplicate DNA sequences flanking the chromosomal transfer DNA) is created as a result of the integration.

Other methods can achieve either or both of these results by integration of a chromosomal transfer DNA into a suitable site on the chromosome. For example, integration of a gene of interest near a promoter on the bacterial chromosome can be designed to result in an operable linkage (for example, by integrating a chromosomal transfer DNA into an operon on the host cell chromosome). The site of integration or sequences adjacent to the site of integration may facilitate amplification (e.g. where the site is located in a transposable element, by providing duplicate DNA sequences, or even by providing a region of DNA sequence homologous to a portion of the chromosomal transfer DNA, thus providing duplicate DNA sequences).

The present invention employs "chromosomal transfer DNA" which may be used to simply, efficiently, and reliably insert a copy of a heterologous gene into the chromosome of a host cell, e.g., E. coli. A chromosomal transfer DNA is a circular DNA comprising one or more copies of a gene encoding a heterologous protein of interest, a selectable marker (e.g., an antibiotic resistance gene), and a recombination site (e.g., a site-specific recombination site such as lambda attP or attB or a DNA sequence homologous to a segment on the host cell chromosome), and lacking an origin of replication or autonomously replicating sequence (ARS). The chromosomal transfer DNA is therefore incapable of replicating independently when introduced in to the host cell. The chromosomal transfer DNA may optionally carry a promoter operably linked to the gene of interest.

When a chromosomal transfer DNA carrying a site-specific recombination site is introduced into a host cell having a chromosome which contains a second, similar recombination site (e.g., another attP or attB site), expression in the host cell of an enzyme which is capable of catalyzing the site-specific recombination of the recombination sites (e.g., integrase) results in the integration of the vector into the host cell chromosome at the recombination site. This site-specific recombination process is much more efficient than general recombination systems acting on homologous vector and host chromosomal sequences and results in integrated sequences having greater stability, particularly when integrase synthesis can be controlled. Integrase may also be provided by a plasmid or other DNA molecule transiently or stably present in the host cell at the time when the chromosomal transfer DNA is introduced.

It will be apparent to one skilled in the art that there are a variety of methods other than the preferred method utilizing attp, attB, and INT which may be used to integrate a chromosomal transfer DNA into the chromosome of a host cell. For example, non-replicating colE1 replicons, transposable elements, or even naked DNA carrying sequences homologous to sequences found on the host chromosome may be used to insert the chromosomal transfer DNA into the host chromosome. The multicopy colicin plasmids ColE1, CloDF13, ColK, and ColA all comprise site-specific recombination systems including a cis- and trans-acting element. For use in the present invention, the cis-acting element from one of these plasmids may be included on the chromosomal transfer DNA and the trans-acting element may be on the chromosomal transfer DNA or provided by the host cell. Transposons, such as the insertion sequence (IS) and Tn3 families of transposons may be used to integrate DNA into the chromosome of a host cell. As with the colicin plasmids described above, the cis-acting transposon elements are included on the chromosomal transfer DNA, while the trans-acting factor may be included on the chromosomal transfer DNA or provided by the host cell. The chromosomal transfer DNA may also carry a DNA sequence homologous to a sequence found on the host cell chromosome, facilitating integration of the chromosomal transfer DNA by homologous recombination. All of these methods fall within the scope of the invention.

An important feature of this approach is that the gene encoding the heterologous protein of interest is at no time operably linked to a functional promoter on a multicopy vector during construction of the transfer DNA. By keeping a functional promoter separated from the gene of interest until immediately before the foreign gene is introduced into the cell at low copy number, the potential toxic or lethal effects of the gene product can be minimized. A toxic foreign gene will not be expressed from a multicopy number plasmid if the gene is not operably linked to a promoter. Other methods for integrating a gene of interest into the host cell chromosome utilize multicopy number plasmids carrying a gene of interest operably linked to a promoter (e.g., Diederich et al. and Weinberg et al.); these genes will be expressed during the propagation of the plasmid, making it extremely difficult, if not impossible, to produce sufficient quantities of the plasmid if the gene of interest is toxic to the host cells in which the plasmid is propagated.

The operable linkage between the gene encoding the heterologous protein of interest and the promoter may be created as a result of the formation of the chromosomal transfer DNA or as a result of integration into the host cell chromosome. In the case where the operable linkage is formed as a result of the formation of the chromosomal transfer DNA, the linkage is created by circularization of the chromosomal transfer DNA. Circularization may be accomplished by, for example, ligation of one or more DNA fragments to form a circular DNA or by homologous recombination into a circular DNA, which would result in circularization of the insert. Preferably, circularization is accomplished by ligation of one or more DNA fragments.

Alternatively, high level expression of less toxic gene products can be accomplished by multiple integrations or by selection for amplification of integrated genes.

Recombinant DNA Methods and Reagents

General techniques for nucleic acid manipulation useful for the practice of the claimed invention are described generally, for example, in Sambrook et al., MOLECULAR CLONING: A LABORATORY MANUAL, Vols. 1–3 (Cold Spring Harbor Laboratory Press, 2 ed., (1989); or F. Ausubel et al., CURRENT PROTOCOLS IN MOLECULAR BIOLOGY (Green Publishing and Wiley-Interscience: New York, 1987) and periodic updates. Reagents useful in nucleic acid manipulation, such as restriction enzymes, T7 RNA polymerase, DNA ligases an so on are commercially available from such vendors as New England BioLabs, Boerhinger Mannheim, Amersham, Promega Biotec, U.S. Biochemicals, and New England Nuclear.

Definitions

"Foreign" or "heterologous" or "non-bacterial;" "native" or "homologous "

A "foreign or "heterologous" polypeptide is a polypeptide which is not normally found in a host cell of a particular species. The nucleic acid encoding such a polypeptide is also referred to as "foreign" or "heterologous." For example, insulin-like growth factor (IGF), insulin-like growth factor binding protein (IGFBP), and transforming growth factor-beta (TGF-β) are native to mammalian cells and human rhinovirus 3C protease is native to viruses and virally-infected mammalian cells, but these proteins are foreign or heterologous to E. coli. A "non-bacterial protein" is a protein or polypeptide which is not naturally found in a bacterial cell. Non-bacterial proteins include viral and eukaryotic proteins. Non-bacterial, foreign, or heterologous proteins may also be fusions between non-bacterial, foreign, or heterologous proteins and other proteins or polypeptides. For the embodiments encompassed by this invention, both "heterologous protein" and "non-bacterial protein" may be expressed. As disclosed herein, genes encoding heterologous or non-bacterial proteins of interest do not contain promoters functional in the host cell. The genes must be linked to a separate promoter that is functional in the host cell in order to be expressed. A "native" or "homologous" polypeptide or DNA sequence, by contrast, is commonly found in the host cell. A promoter or other sequence effecting, for example, the transcription or translation of a gene is also considered "homologous" if it is functional in the host cell. For example, a T7 promoter is considered "homologous" to an E. coli host cell, since, if T7 RNA polymerase is present in the cell, the T7 promoter is capable of driving the transcription of a polypeptide-encoding sequence to which it is operably linked.

"Genes encoding heterologous, foreign or non- bacterial proteins""Genes encoding heterologous, foreign or non-bacterial proteins" contain all of the genetic elements necessary for the expression of the heterologous, foreign or non-bacterial protein with the exception of a promoter functional in the host cell. These genes encompass recombinant genes which may include genetic elements native to the host cell. Further, the coding regions of these genes may optionally be optimized for the codon usage of the host cell.

"Encode" A nucleic acid is said to "encode" a polypeptide if, in its native state or when manipulated by recombinant DNA methods, it can be transcribed and/or translated to produce the polypeptide.

"Operably linked" A nucleic acid sequence is operably linked when it is placed into a functional relationship with another nucleic acid sequence. For example, a promoter is operably linked to a coding sequence if the promoter affects its transcription or expression. Generally, DNA sequences which are operably linked are contiguous and, where necessary, in reading frame.

"Recombinant" A "recombinant" nucleic acid is one which is made by the joining of two otherwise separated segments of nucleic acid sequence in vitro or by chemical synthesis.

"Chromosomal amplification""Chromosomal amplification" refers to the increase in copy number of a DNA sequence on the host chromosome. Chromosomal amplification does not refer to extrachromosomal amplification such as replication of multicopy number plasmids or in vitro amplification such as the polymerase chain reaction (PCR).

Probes and primers

Nucleic acid probes and primers are isolated nucleic acids, generally single stranded, and, especially in the case of probes, are typically attached to a label or reporter molecule. Probes are used, for example, to identify the presence of a hybridizing nucleic acid sequence in a tissue or other sample or a cDNA or genomic clone in a library. Primers are used, for example, for amplification of nucleic acid sequences, e.g., by the polymerase chain reaction (PCR). The preparation and use of probes and primers is described, e.g., in Sambrook et al., supra or Ausubel et al. supra.

Chemical synthesis of nucleic acids

Nucleic acids, especially short nucleic acids such as amplification primers, may be produced by chemical synthesis, e.g., by the phosphoramidite method described by Beaucage and Carruthers (1981) Tetra. Letts. 22:1859–1862 or the triester method according to Matteucci et al. (1981) J. Amer. Chem. Soc. 103:3185, and may be performed on automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Features of chromosomal transfer DNA and of plasmids used in their construction

Chromosomal transfer DNA comprises a DNA fragment encoding a selectable marker and a sequence encoding a desired heterologous polypeptide. Optionally, a chromosomal transfer DNA may also comprise, in an operable linkage to the sequence encoding the desired heterologous polypeptide, transcription and translation initiation regulatory sequences and expression control sequences, which may include a promoter, an enhancer and necessary processing information sites, such as ribosome-binding sites, and mRNA stabilizing sequences, as well as any necessary secretion signals, where appropriate, which allow the protein to cross and/or lodge in cell membranes, and thus attain its functional topology, or be secreted from the cell.

Plasmids used in construction of a chromosomal transfer DNA will also typically comprise a replication system recognized by the host, including an origin of replication or autonomously replicating sequence (ARS). In the case where a plasmid used in the construction of a chromosomal transfer DNA carries duplicate DNA sequences, the plasmid may be propagated in a $rec^{31}$ host cell. Preferably, $rec^-$ host cells are used for propagation of plasmids used to create chromosomal transfer DNAs and plasmids carrying components of chromosomal transfer DNAs when these plasmids carry duplicate DNA sequences, and are not generally utilized as host cells for integration of chromosomal transfer DNAs.

Chromosomal transfer DNA may be prepared from such vectors by means of standard recombinant techniques well known in the art and discussed, for example, in Sambrook et al., supra or Ausubel et al. supra.

An appropriate promoter and other sequences necessary for efficient transcription and/or translation are selected so as to be functional in the host cell. Examples of workable combinations of cell lines and expression vectors are described in Sambrook et al., supra or Ausubel et al., supra; see also, e.g., Metzger et al. (1988) Nature 334:31–36. Promoters such as the trp, lac and phage promoters (e.g., T7, T3, SP6), tRNA promoters and glycolytic enzyme promoters are useful in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and other. See, e.g., Hitzeman et al. EP 73,657A. Appropriate mammalian promoters include the early and late promoters from SV40 (Fiers et al. (1978) Nature 273:113) or promoters derived from murine Moloney leukemia virus, mouse mammary tumor virus, avian sarcoma viruses, adenovirus II, bovine papilloma virus or polyoma virus. In addition, the construct may be joined to an amplifiable gene (e.g., DHFR) so that multiple copies of the gene may be made, where desired. For appropriate eukaryotic enhancer and other expression control sequences see, e.g., ENHANCERS AND EUKARYOTIC GENE EXPRESSION (Cold Spring Harbor Press, New York, 1983).

It is preferable that the promoter driving expression of the heterologous gene when integrated in the chromosome of the host is controllable.

Chromosomal transfer DNAs and plasmids employed in their construction generally comprise a selectable marker, a gene encoding a protein necessary for the survival or growth of a host cell transformed with the chromosomal transfer DNA or plasmid. Typical selectable markers (a) confer resistance to antibiotics or other toxic substances, e.g. ampicillin, neomycin, methotrexate, etc.; (b) complement auxotrophic deficiencies; or (c) supply critical nutrients not available from complex media, e.g. the gene encoding D-alanine racemase for Bacilli. The choice of the proper selectable marker will depend on the host cell.

The chromosome transfer DNAs of the present invention may contain a site-specific recombination site, such as the phage lambda attP site. When transformed into a bacterial host strain (such as $E.$ $coli$ B1384) which makes the enzyme integrase, integrase recognizes the attP site on the chromosomal transfer DNA and catalyses its recombination with an att site (integrase can catalyze a recombination between two attP and attB or two attP sites). Bacterial host cells bearing the integrated DNA are selected for on the basis of a selectable marker carried on the integrated DNA.

Thus, integration utilizing site-specific recombination generally involves expression of an enzyme such as integrase which can catalyze site-specific recombination and the presence of a site recognized by the enzyme on both the chromosomal transfer DNA and the bacterial chromosome. Other site-specific recombination systems characterized by an "integrase" or similar enzyme and sites specifically recognized by the "integrase" could be used as well.

High level expression of a foreign gene integrated into the chromosome of a host cell in multiple copies is also possible, e.g., by incorporating multiple att sites in the host cell chromosome and introducing multiple chromosomal transfer DNAs into the host cell. Additionally or alternatively, host cells containing multiple copies of the integrated DNA may be obtained by selecting for chromosomal amplification. Chromosomal amplification is facilitated when the selectable marker is flanked by duplicate DNA sequences. Preferably, the duplicate DNA sequences flank a first and a second selectable marker. The first selectable marker is effective at low copy number and can be used to select for integration of the chromosomal transfer DNA. The second selectable marker is preferably effective only at high copy number. Following selection for integration using the first selectable marker, the second selectable marker is then used to select for host cells which contain multiple copies of the integrated DNA.

An important feature of the chromosomal transfer system of the present invention is that the gene encoding the heterologous protein is not expressed before integration; it is not operably linked to a promoter until either (a) the transfer DNA is constructed in vitro or (b) the chromosomal transfer DNA is integrated into the host cell chromosome. This approach allows one to employ high copy number plasmids as DNA sources in constructing the chromosomal transfer DNA. High copy number plasmids carrying a toxic heterologous gene are often difficult to propagate when the toxic gene is operably linked to a promoter. Low copy number plasmids are more difficult to work with in the laboratory. For example, DNA minipreps may produce inadequate DNA for in vitro manipulations. The chromosomal transfer DNA is constructed from one or more DNA sources by circularization of selected DNA fragments.

When a single DNA is used to construct the chromosomal transfer DNA, both the gene encoding the heterologous protein of interest and the promoter are located on the same DNA, however the gene and promoter are not operably linked. This may be accomplished by, for example, placing the promoter and gene of interest on either side of a spacer DNA sequence which blocks any operable linkage (for example, by including a terminator sequence). Preferably, this intervening DNA sequence also includes any other portions of the source DNA which must be removed for creation of the chromosomal transfer DNA, such as an origin of replication or ARS. The chromosomal transfer DNA is constructed by deleting the DNA sequence which blocks the operable linkage between the gene and the promoter, then circularizing the remaining DNA.

Figure 6:
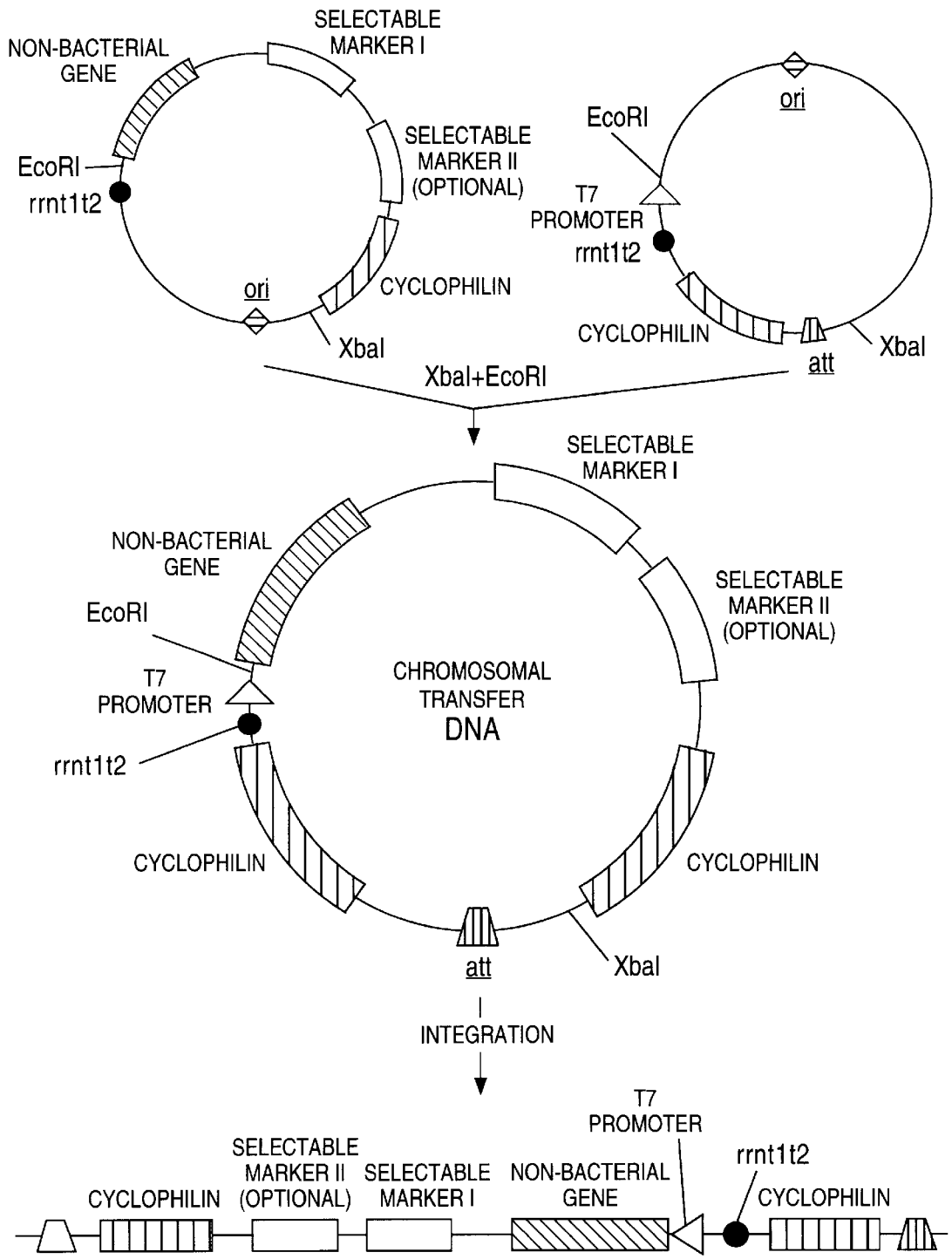
FIGS. 6–9 show diagrammatically the general strategy for construction of chromosomal transfer DNA's.

There are several methods by which one may construct a chromosomal transfer DNA using two or more DNA sources. In one preferred embodiment, diagramed in FIG. 1, one DNA source contains the gene encoding the heterologous protein, which is not expressed since it is not operably linked to a promoter. A second DNA source contains the promoter to which the gene encoding the heterologous protein will be operably linked on the chromosomal transfer DNA. Appropriate cleavage will result in two DNA fragments, one carrying the foreign gene, the other carrying the promoter, and either of the fragments carrying other necessary sequences, such as selectable markers and sequences necessary for integration into the host cell chromosome. The two DNA fragments are then joined together, such that an operable linkage is formed between the promoter and the gene encoding the heterologous protein of interest. A variation of this embodiment, shown schematically in FIG. 6, further includes two copies of a gene, one copy of which is located on each of the two plasmids. The chromosomal transfer DNA created by ligation of fragments of these two plasmids includes the gene encoding the heterologous protein of interest operably linked to the promoter, two copies of the gene, selectable marker(s), and any sequences necessary to integrate the chromosomal transfer DNA into the chromosome of the host cell. In this embodiment, the two copies of the gene flank the gene encoding the heterologous protein of interest and selectable marker(s), facilitating amplification of the integrated DNA.

Figure 7:
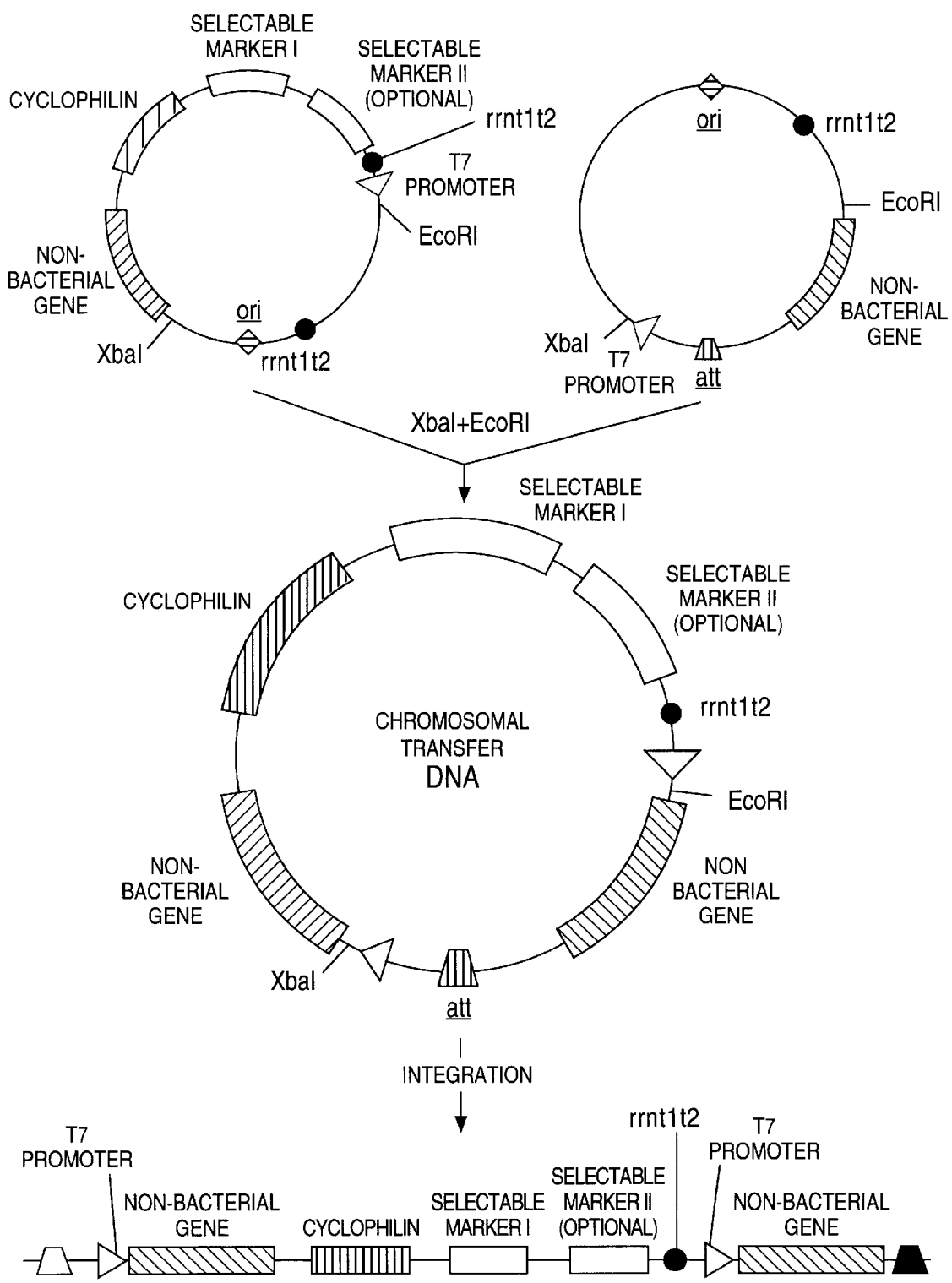

Another preferred embodiment, shown in FIG. 7, also uses two DNA sources. In this embodiment, each of the two DNA sources carries a copy of the gene encoding the heterologous protein of interest and the promoter, but the gene encoding the heterologous protein of interest and promoter are not operably linked on either DNA source. As with the previously described embodiment, other necessary sequences may be carried by either DNA source (alternatively the other necessary sequences may be provided by one or more accessory DNA sources). The two DNA sources are cleaved, then joined to each other, forming a circular chromosomal transfer DNA which has two copies of the foreign gene, each operably linked to a copy of a promoter. The promoter from the first DNA source is operably linked to the gene encoding the heterologous protein of interest from the second DNA source, and the promoter from the second DNA source is operably linked to the gene encoding the heterologous protein of interest from the first DNA source.

Figure 8:
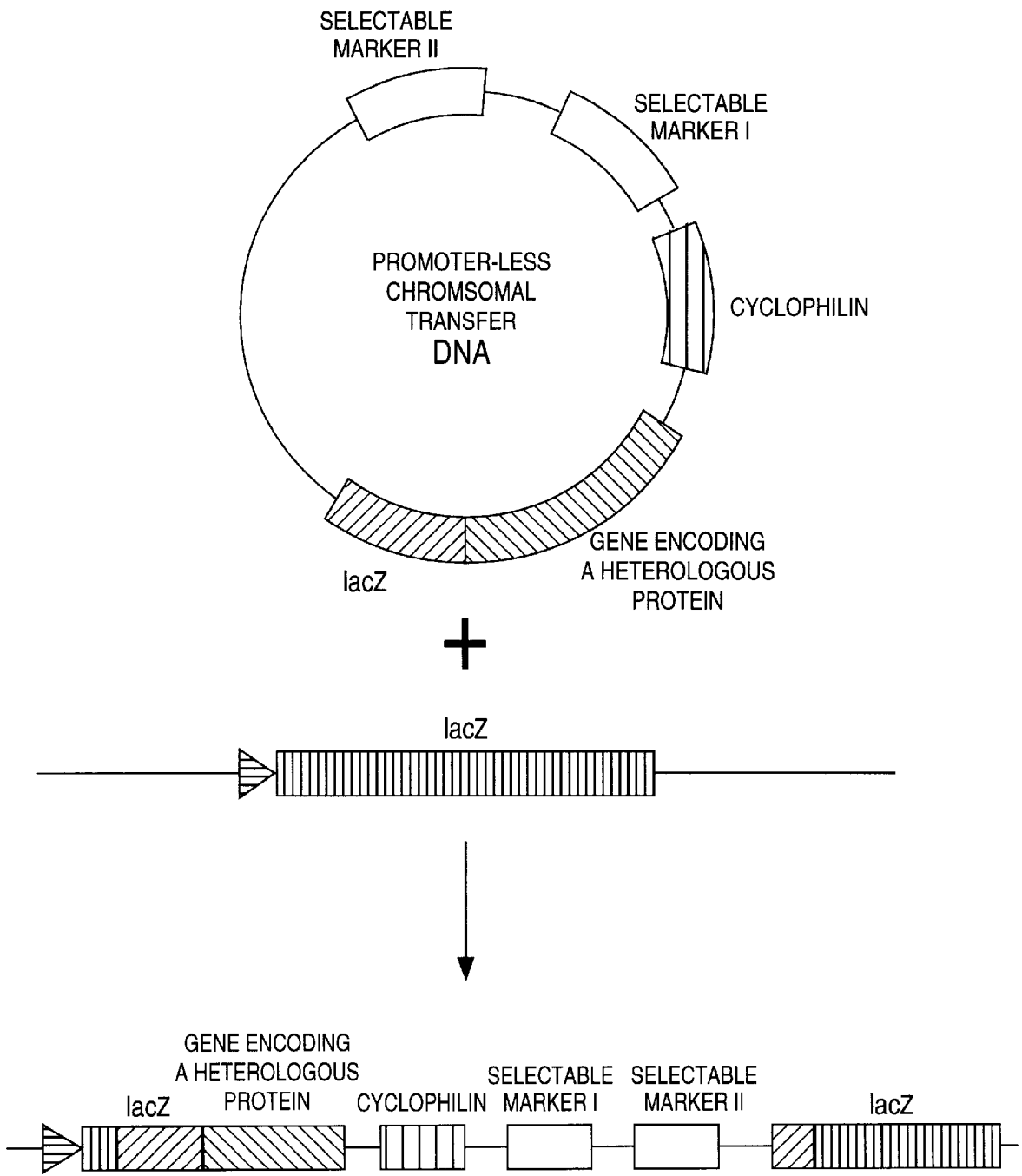
Figure 9:
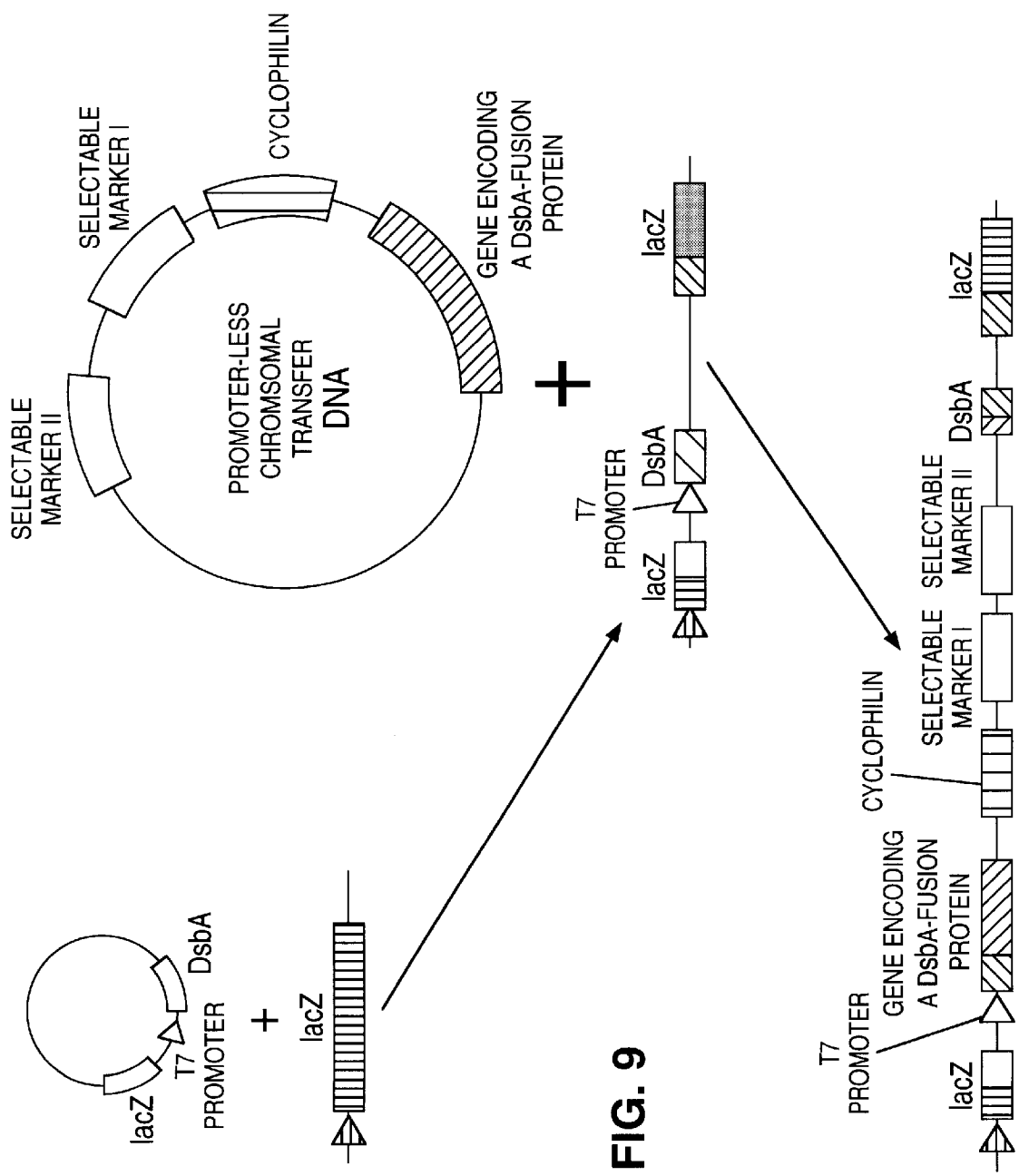
Figure 10:
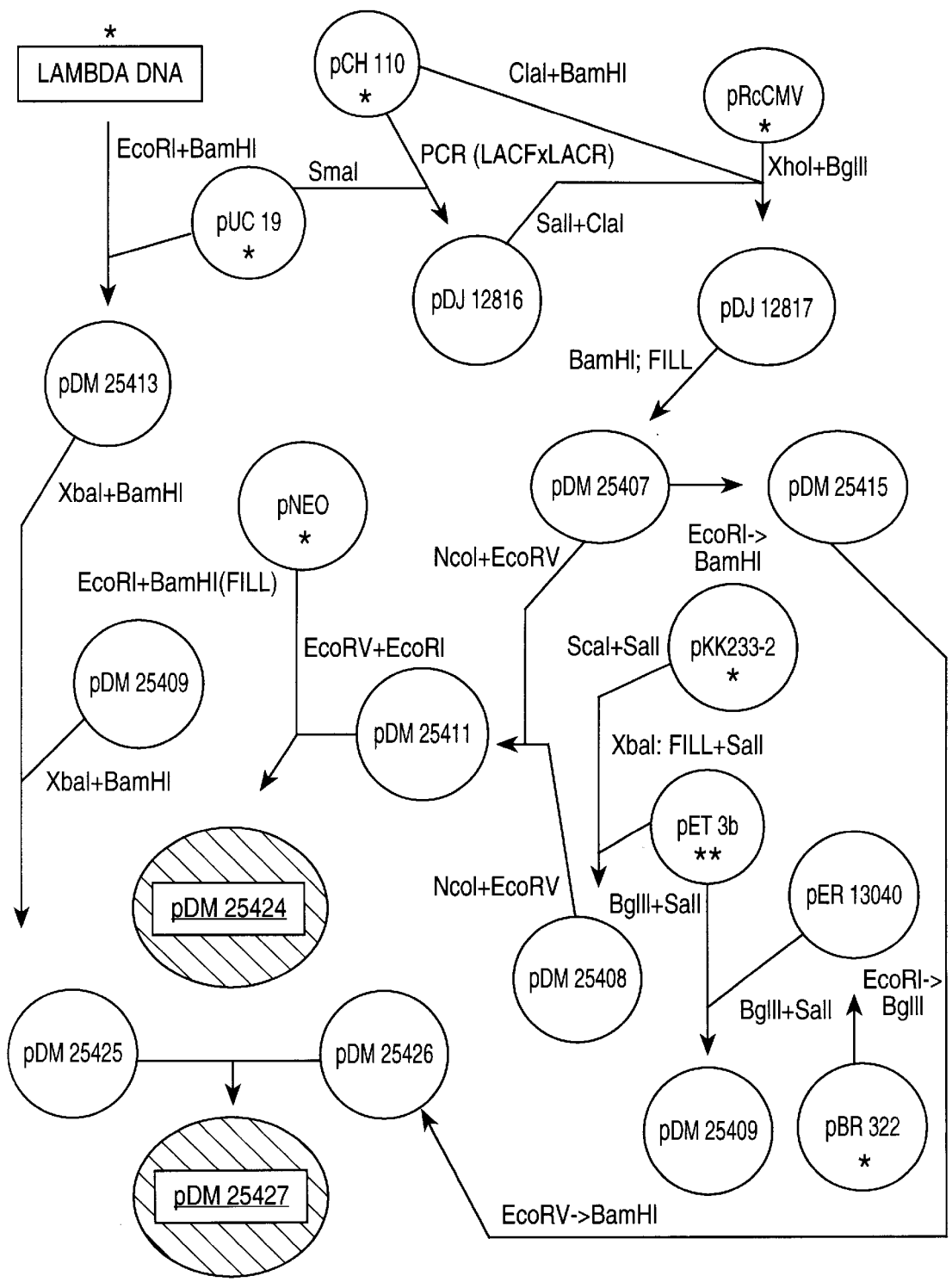
FIGS. 10–13 show the plasmid genealogy of chromosomal transfer DNAs.
Figure 11:
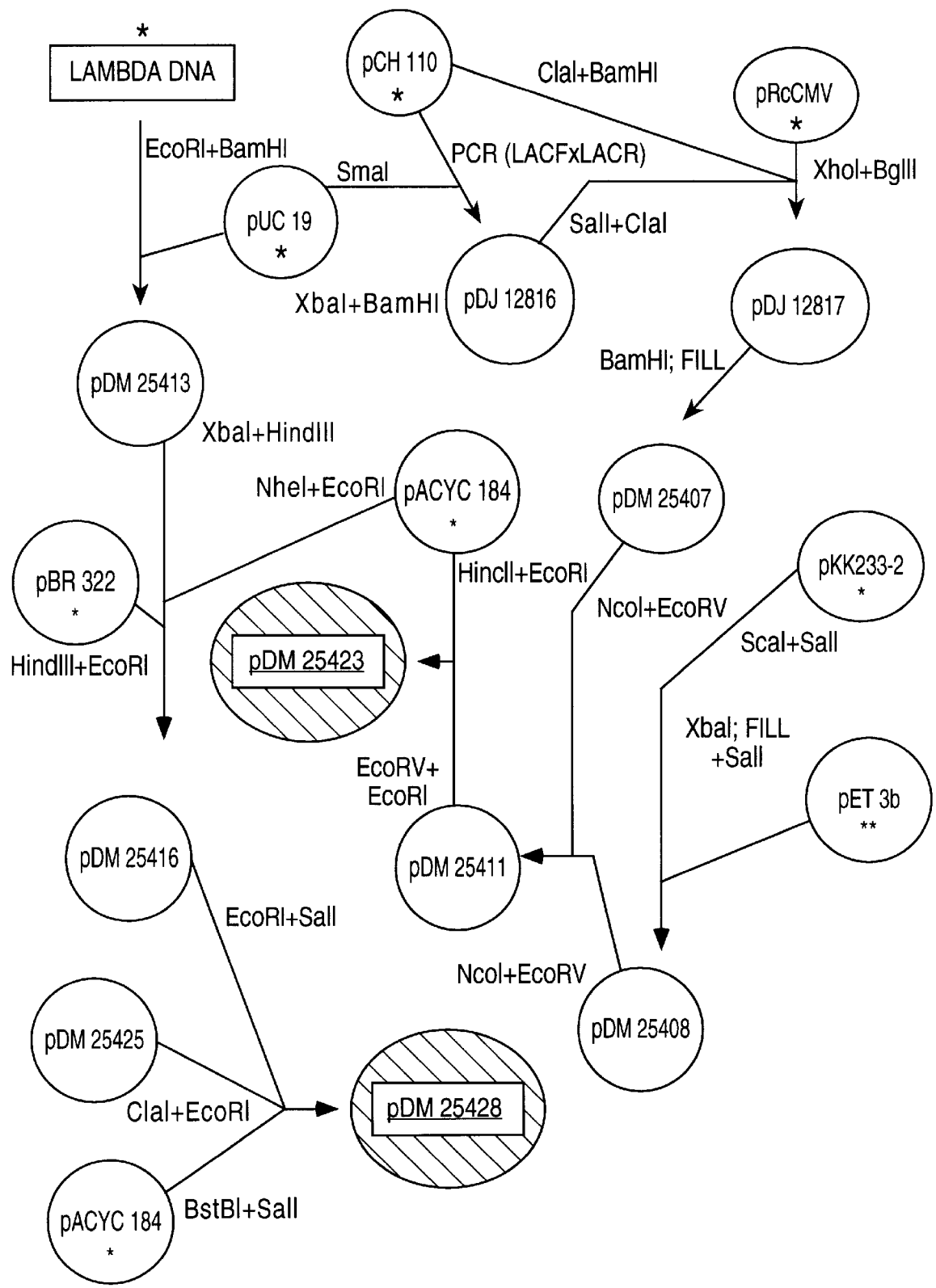

Chromosomal transfer DNAs may also be designed without promoters (FIGS. 8 and 9). These promoter-less chromosomal transfer DNAs are integrated into target sites on the bacterial chromosome which place the gene encoding the heterologous protein of interest into an operable linkage with a promoter on the host cell chromosome. The chromosomal transfer DNA of this embodiment includes a copy of a gene encoding a heterologous protein of interest linked in-frame to a segment of target-site DNA segment homologous to DNA on the host cell chromosome and a selectable marker. This target site DNA sequence will typically be the 5' end of a gene located on the bacterial chromosome downstream from a promoter. Integration of the chromosomal transfer DNA into the host cell chromosome will place the gene encoding the heterologous protein of interest into operable linkage with a bacterial promoter. The target sequence on the host cell chromosome may be a naturally occurring sequence or may be a site which is introduced into the chromosome of the host cell. A target may be introduced into the chromosome of a host cell utilizing a DNA sequence homologous to a segment of the host cell chromosome, as described above for integration of the chromosomal transfer DNA. A target site may also be introduced using site-specific recombination, such as the attB/attP/INT system described above. A target site sequence is at least about 10 bases long, preferably at least about 30 bases long, and most preferably at least about 100 bases long. The DNA sequence on the chromosomal transfer DNA and the target site are at least about 80% homologous, preferably at least about 90% homologous, and most preferably at least about 95% homologous. A target site is preferably rare in the host cell chromosome and, more preferably, is unique in the host cell chromosome. Integration of the chromosomal transfer DNA using a sequence homologous to a segment on the host cell chromosome facilitates amplification of the integrated DNA by placing duplicate DNA sequences flanking the integrated DNA (see FIGS. 8 and 9).

Introducing DNA into host cells

A variety of methods for introducing nucleic acids into host cells are known in the art, including, but not limited to, electroporation; transfection employing calcium chloride, rubidium chloride calcium phosphate; DEAE-dextran, or other substances; microprojectile bombardment; lipofection; and infection (where the vector is an infectious agent, such as a retroviral genome). See generally, Sambrook et al., supra and Ausubel et al., supra.

Host cells

The methods of the present invention are preferably used with prokaryotic host cells, although they would be applicable to eukaryotic host cells as well. Among prokaryotic hosts, gram negative bacteria are preferred, especially *Escherichia coli*. Other prokaryotes, such as *Bacillus subtilis* or Pseudomonas may also be used.

Mammalian or other eukaryotic host cells, such as yeast, filamentous fungi, plant, insect, amphibian or avian species may also be used. See, TISSUE CULTURe (Kruse and Patterson, ed., Academic Press, 1973). Useful mammalian host cell lines include, but are not limited to, VERO and HeLa cells, Chinese hamster ovary (CHO) cells, and W138, BHK, and COS cell lines.

Amplification of Integrated DNA

Amplification of integrated genes can be efficiently accomplished by any of several methods, for example, chromosomal duplication or replicative transposition. Integrated DNA which contains or is flanked by duplicate DNA sequences of 25 or more base pairs will form chromosomal duplications (Normark et al. (1977) *J. Bacteriol.* 132:912–922; Edland et al. (1979) *Mol. Gen. Genet.* 173:115–125; Tlsty et al. (1984) *Cell* 37:217–224; Stern et al. (1984) *Cell* 37:1015–1026). Selection for duplications (amplification) is greatly facilitated if the duplicate DNA contains a selectable marker, such as an antibiotic resistance gene or a gene which complements a host cell deficiency. Preferably the integrated DNA includes two selectable markers; a first selectable marker which is operable at low copy number and is used to select for integrants, and an second selectable marker which requires high copy number and is used to select for host cells which have amplified the integrated DNA. Amplification may also be accomplished by replicative transposition, in the case where the chromosomal transfer DNA contains the appropriate transposon sequences or the chromosomal transfer DNA is integrated into a transposon. Preferably, amplification is accomplished by selection for chromosomal duplications.

Production of non-bacterial proteins

Following integration of the chromosomal transfer DNA into the host cell chromosome, and optionally following amplification of the integrated DNA, the foreign gene may be expressed, resulting in the production of the non-bacterial protein of interest. It is preferable that the promoter controlling expression of the integrated gene be controllable (i.e., inducible), so that any toxic effects of the gene product can be minimized. Following expression of the foreign gene, the protein product may be purified. As will be apparent to one skilled in the art, the purification method used will depend on the identity of the foreign protein.

The invention will be better understood by reference to the following examples, which are intended to merely illustrate the invention. The scope of the invention is not to be considered limited thereto.

EXAMPLES

Example 1

Integration of a chromosomal transfer DNA comprising a foreign gene into the chromosome of *E. coli* strain B1384

Figure 2:
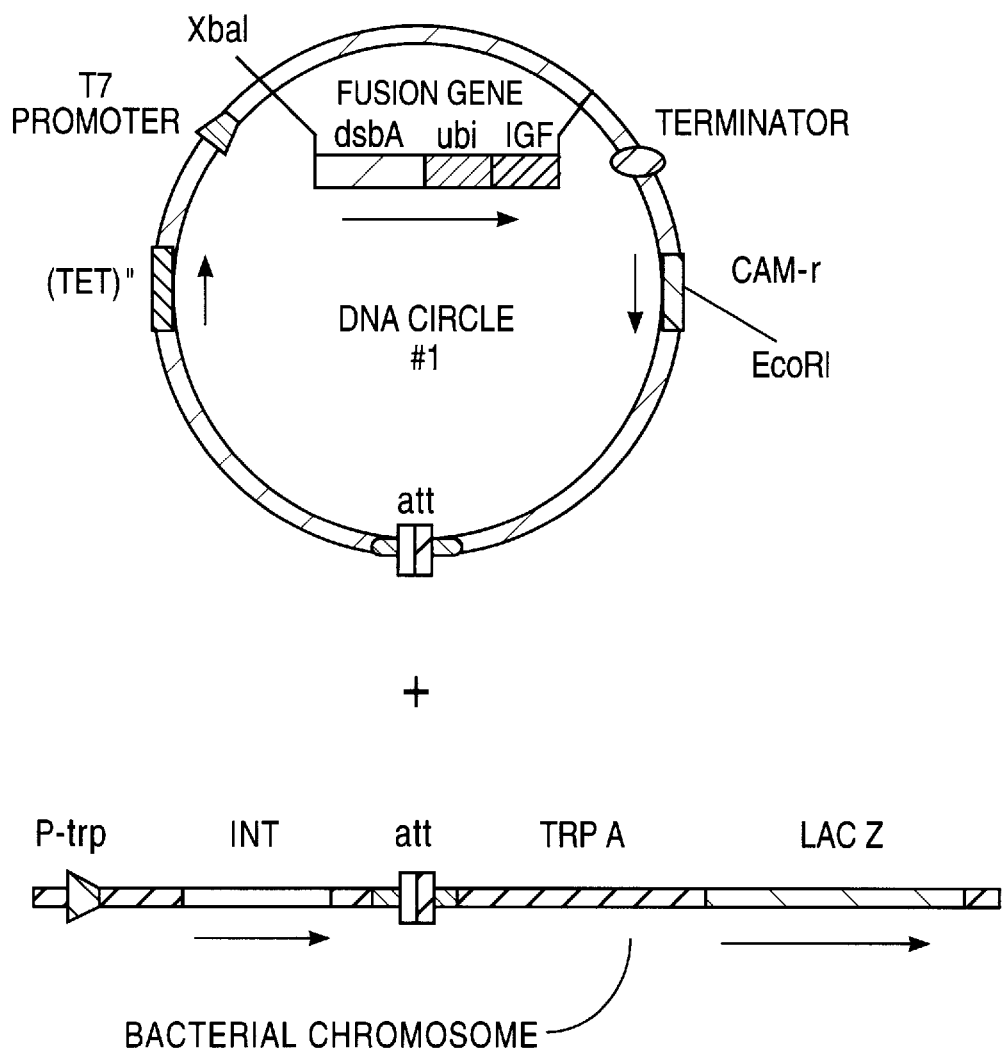
FIG. 2 shows a chromosomal transfer DNA formed from the ligation of two DNA fragments. One of the fragments contains a fusion gene comprising sequences encoding *E. coli* DsbA, yeast ubiquitin (beginning with a Met), and human insulin-like growth factor I ("dsbA-ubi-IGF") (not beginning with a Met), as discussed in co-owned, co-pending U.S. patent application Ser. No. 08/100,744, filed Aug. 2, 1993. The other DNA fragment contains a T7 promoter. Both the chromosomal transfer DNA and the bacterial chromosome contain a recombination site from phage lambda, att P. The chromosomal transfer DNA is transformed into *E. coli* strain B1384, which makes integrase (INT) under the control of the trp promoter (P-trp). Integrase catalyzes site-specific integration of the chromosomal transfer DNA into the bacterial chromosome at the att site. The trp promoter can be induced during transformation by adding 1 mM indole acrylic acid (IAA) to the medium. Cells with integrated chromosomal transfer DNA sequences are resistant to chloramphenicol (CAM-r, 10 µg/ml).

The general strategy for integrating a chromosomal transfer DNA comprising a foreign gene into the chromosome of *E. coli* is depicted schematically in FIG. 1. Two plasmids were constructed: pDM25432 contained a foreign gene of interest (in this example, an IGF-I fusion gene) lacking an operably linked bacterial promoter; pDM25423 contained a T7 promoter. By ligating restriction fragments purified from each of these vectors, a DNA circle lacking an origin of replication —chromosomal transfer DNA—was generated. This chromosomal transfer DNA contained an antibiotic resistance gene which affords resistance to chloramphenicol (CAM-r) and a site-specific recombination site from phage lambda, attP. This chromosomal transfer DNA is transformed into a bacterial strain such as *E. coli* B1384 (Mascarenhas et al. (1983) Virology 124:100–108) (FIG. 2), which makes the enzyme integrase (INT) under the control of the trp promoter, which can be induced during transformation by adding 1 mM indole acrylic acid (IAA) to the medium. B1384 also contains an att P in its chromosome. Integrase recognizes the att P sites on the chromosomal transfer DNA and in the chromosome of B1384 and catalyses their recombination, leading to the site-specific integration of the chromosomal transfer DNA into the bacterial chromosome at the att P site (Weisberg et al. *Comprehensive Virology*, vol. 8, pp. 197–258 (Plenum, Fraenckel-Conrat and Wagner, eds., New York, N.Y., 1977). Bacterial host cells bearing the integrated DNA are selected for on the basis of their resistance to chloramphenicol.

Figure 3:
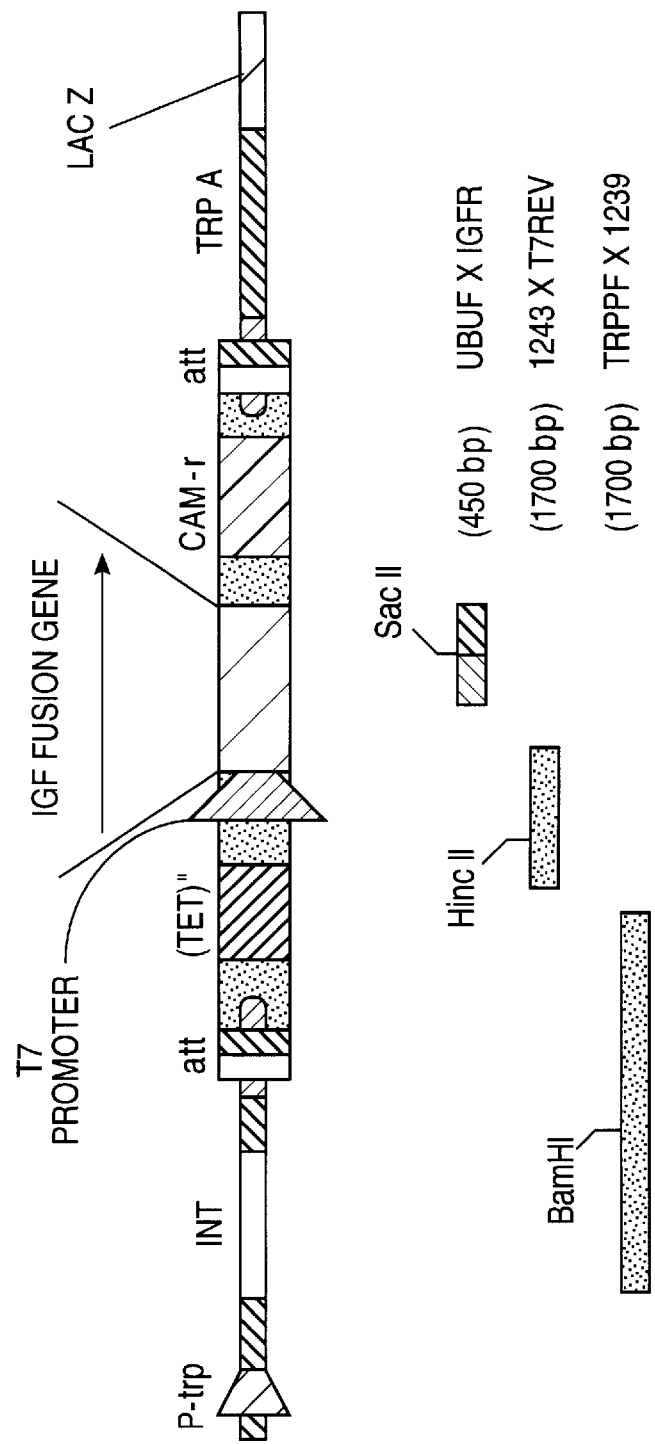
FIG. 3 shows a B1384 chromosomal integrant resulting from the process described in FIG. 2. The integration can be confirmed by amplifying host chromosomal DNA by PCR with various primer sets (e.g., UBUFxIGFR, 1243xT7REV, or TRPPFx1239), digesting the amplified fragments with the appropriate restriction enzyme (SacII, HincII, or BamHI, respectively), and sizing the products by gel electrophoresis).

Chloramphenicol-resistant chromosomal integrants were tested as summarized in FIG. 3. The presence of the integrated chromosomal transfer DNA was confirmed by amplifying host chromosomal DNA by PCR with the following primer sets (e.g., UBUF×IGFR, 1243×T7REV, or TRPPF×1239)

IGFR: 5'... CCC ATC GAT GCA TTA AGC GGA TTT AGC CGG TTT CAG .... 3' (SEQ ID NO:1)

1239: 5'... GCC TGA CTG CGT TAG CAA TTT AAC TGT GAT ... 3'( SEQ ID NO:2)

1243: 5;... CTG GGC TGC TTC CTA ATG CAG GAG TCG CAT ... 3' (SEQ ID NO:3)

1227: 5'... TAA TAC GAC TCA CTA TAG GGA GA ... 3' (SEQ ID NO:4)

TRPPF: 5'... GAT CTG TTG ACA ATT AAT CAT CGA ACT AGT TAA CTA GTA CGC AAG TT ... 3' (SEQ ID NO:5)

T7REV: 5'... TGC TAG TTA TTG CTC AGC GG ... 3' (SEQ ID NO:6)

CYCF1: 5'... CAG GAT CCG ATC GTG GAG GAT GAT TAA ATG GCG AAA GGG GAC CCG CAC ... 3' (SEQ ID NO:7)

CYCR1: 5'... CAG GAA GCT TAC GGC AGG ACT TTA GCG GAA AG ... 3' (SEQ ID NO:8)

UBUF: 5'... GGG GCC GCG GTG GCA TGC AGA TTT TCG TCA AGA CTT TGA ... 3' (SEQ ID NO:9)

The amplified fragments were digested with the appropriate restriction enzyme (SacII, HinCII, or BamHI, respectively). The products were sized by agarose gel electrophoresis. Presence of the integrated sequences was demonstrated by amplification of:

chromosomal ubiquitin and IGF sequences, demonstrating the presence of the relevant foreign gene;

chromosomal tet and T7 sequences, demonstrating the juxtaposition of the T7 promoter and the fusion gene; and adjacent chromosomal trp and tet sequences, demonstrating insertion of the chromosomal transfer DNA at the expected location.

The chromosomal integration of the chromosomal transfer DNA was also confirmed by the following evidence:

resistance of the bacterial host to chloramphenicol;

no plasmid DNA in DNA minipreps;

lack of beta-lactamase enzymatic activity, confirming the absence of the parental plasmids (beta-lactamase was assayed using a chromogenic substrate, 7-thienyl-2-acetamido-3-2-4 n,n-dimethylaminphenylazopyridiniummethyl-3ceph em-4 carboxylic acid (PADAC), as described in ENZYME INHIBITORs pp. 169–177 (Verlage Chemie, Broderick, V., ed.); and segregation analysis: Isolates were grown in L broth with or without 1 mM IAA at 37° C. overnight and plated on LB agar plates. Single colonies from each culture were tested for retention of chloramphenicol resistance. 100% retention was observed from cultures without IAA; 11% retention was observed in cultures with IAA.

Six of seven isolates tested showed the expected phenotypes.

B1384 does not contain the gene for T7 RNA polymerase. In order to test the expression of the chromosomal constructs, P1 lysates were prepared on each of the six strains carrying the integrated DNA and used to transduce strain W3110DE3 to chloramphenicol resistance (A SHORT COURSE IN BACTERIAL GENETICS: A LABORATORY MANUAL AND HANDBOOK FOR ESCHERICHIA COLI AND RELATED BACTERIA (Cold Spring Harbor Laboratory Press, Miller, J. H., ed., 1992)). Strain W3110DE3 carries the T7 RNA polymerase gene under the control of the lac promoter. It is also Gal$^+$, unlike B1384. Transductants were therefore selected on galactose minimal plates containing 20 μg/ml chloramphenicol. Single colonies from each transduction experiment (independent donors) were purified and tested further.

The results obtained were identical in all six independent cases: the chromosomal transfer DNA was transferred with high efficiency to a new location on the bacterial chromosome, the att sites flanking the prophage in W3110DE3. This was confirmed by chloramphenicol resistance;

no plasmid DNA in DNA minipreps;

i21 immunity (DE3 lysogen; phage lysates were plated on bacterial lawns by standard techniques);

gal$^+$(i.e. growth on galactose minimal plates);

expression of IGF protein under lac control (expression and analysis carried out as described in Example 1 or co-owned, co-pending U.S. patent application Ser. No. 08/101,506, filed Aug. 2, 1993).

Chromosomal DNA from the six strains ("integrants") was digested to completion with BglII and NcoI and a Southern blot of the digested DNA was probed with a labeled 0.6 kb DsbA DNA probe which covers the entire gene sequence coding for mature DsbA (Bardwell et al. (1991) Cell 67:581–589; see also Kamitani et al. (1992) EMBO J 11:57–62). Each of the six integrants contained insertions; the blots demonstrated the existence of several double insertions, one single insertion, and one (isolate WB3–6) apparently duplicate double (i.e. triple) insertion.

Figure 4:
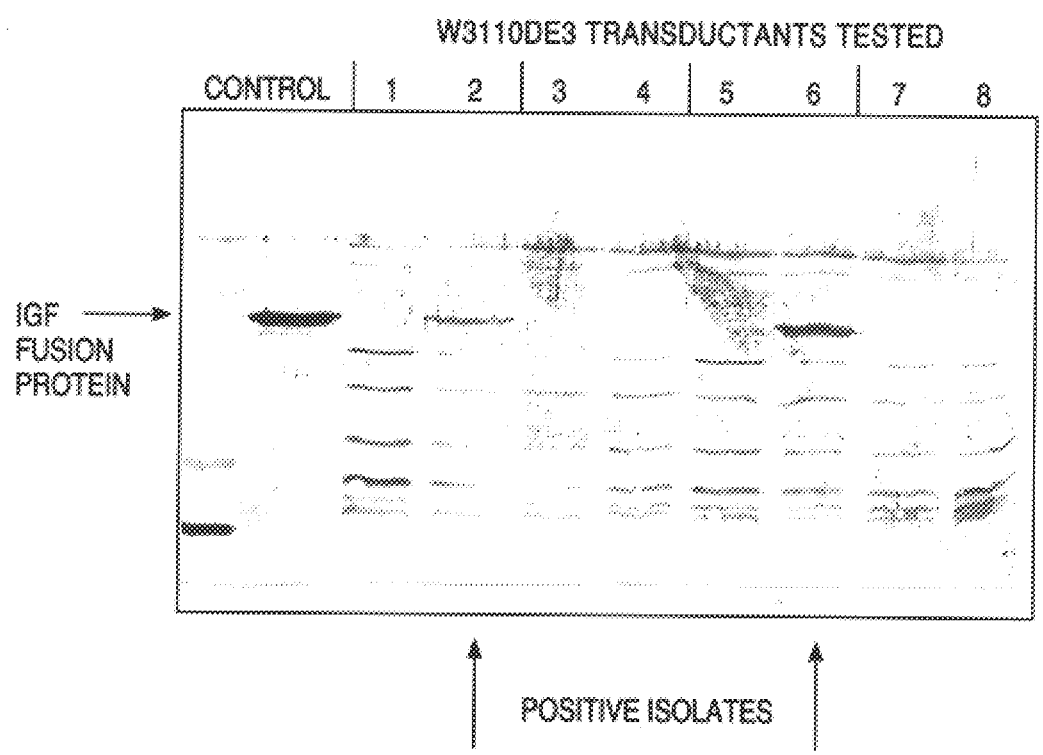
FIG. 4 shows a Western blot of whole cell lysates of chloramphenicol resistant W3110DE3 transductants. Also included are protein size markers (far left lane) and IGF fusion protein (control).

The six integrants were tested for expression of the IGF fusion protein after induction with isopropyl-β-thiogalactopyranoside (IPTG). Cells were induced with IPTG for two hours and whole cell extracts for the induced integrants, as well as size markers and an IGF fusion protein control, were separated by 12% SDS-PAGE, Western blotted, and reacted with polyclonal anti-IGF sera (see Example 1 of co-owned, co-pending U.S. patent application Ser. No. 08/101,506, filed Aug. 2, 1993) (FIG. 4). Isolate WB3–6 (FIG. 4, lane 6) showed the highest levels of expression of the IGF fusion protein. An induced band of the same size was also seen on Coomassie blue-stained gels.

Figure 5:
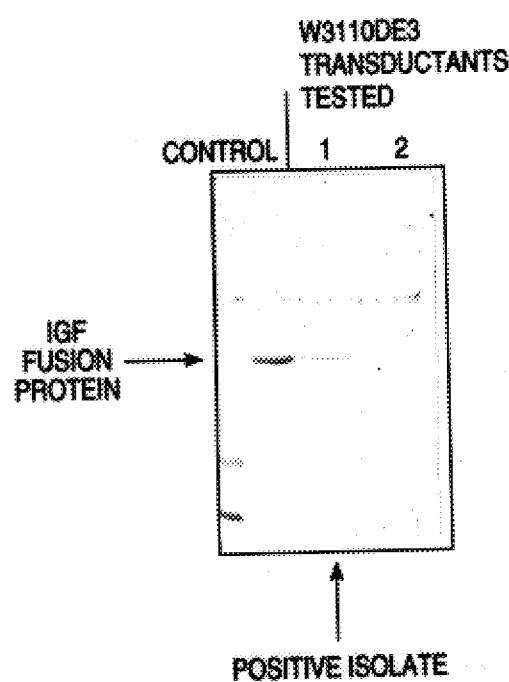
FIG. 5 shows a Western blot of whole cell lysates of kanamycin resistant transductants.

A different binary system was used to generate a chromosomal transfer DNA carrying a kanamycin resistance marker. The plasmids used, pDM25424 and pDM25427, are described in the figures. The configuration and location of the insert were confirmed by PCR, giving results which were virtually identical to those described above. After transduction into the W3110DE3 background, several individual isolates were obtained which expressed the IGF fusion protein at level that could be easily detected by Western blotting (FIG. 5). Procedures used were identical to the ones described above for the chloramphenicol-resistant isolates, except that the antibiotic and resistance gene were kanamycin instead of chloramphenicol. Purified fusion protein was the control. Lanes 1 and 2 contain whole cell lysates from two transducted isolates.

The construction of the vectors employed in the two binary systems is summarized in FIGS. 10–13. The sources for the plasmids employed were: pBR322, pUC18, pUC19, pKK233-2, ptRC99A, pCH110, and PNEO (Pharmacia, Piscataway, N.J.); pLG339HLY (Dr. Barry Holland, Institute de Génétiques et Microbiologie, Université Paris-Sud); pRc-CMV (Invitrogen, San Diego, CA); pACYC177 and pACYC184 (New England BioLabs, Beverly, MA); pET3b (Studier and Moffat (1986) *J. Mol. Biol.* 189:113–130); pYZ22070 (described in Example 1 of co-owned, co-pending U.S. patent application Ser. No. 08/101,744, filed Aug. 2, 1993).

*E. coli* K-12 strain W3110 was obtained from B. Bachmann, ECGSC, Yale University. It was lysogenized with the DE3 defective phage as described by Studier and Moffat (1986) *J. Mol. Biol.* 198:113–130. W3110DE3 was one such lysogen. The cyclophilin gene was amplified by the polymerase chain reaction (PCR) from W3110 using the primers CYCF1 and CYCRI (see above).

Example 2
Chromosomal expression of a DsbA::ubiquitin::IGF-I fusion gene

A DsbA::ubiquitin::IGF-I fusion gene was assembled and integrated into the chromosome of bacterial host cells with a chromosomal transfer DNA produced using the double-cassette binary system. The strategy for constructing the double cassette binary system vectors is shown in FIG. 14.

Figure 12:
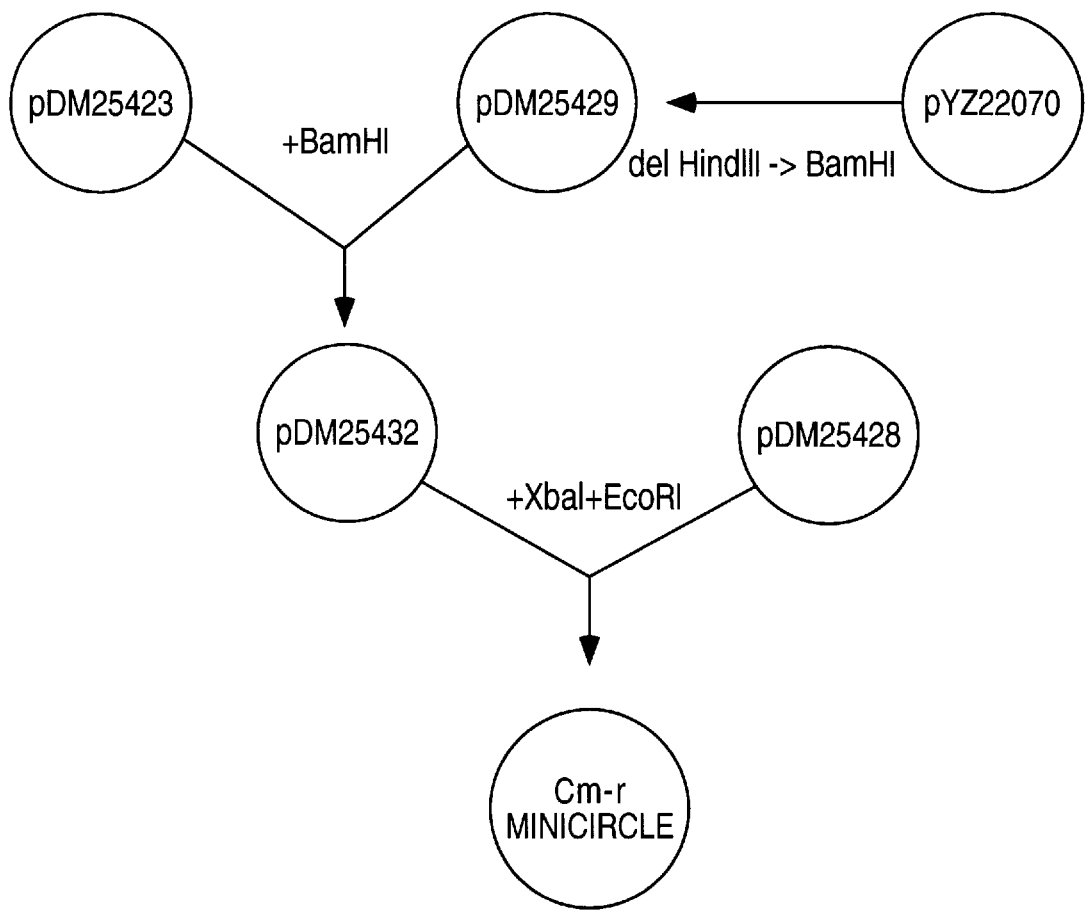
Figure 13:
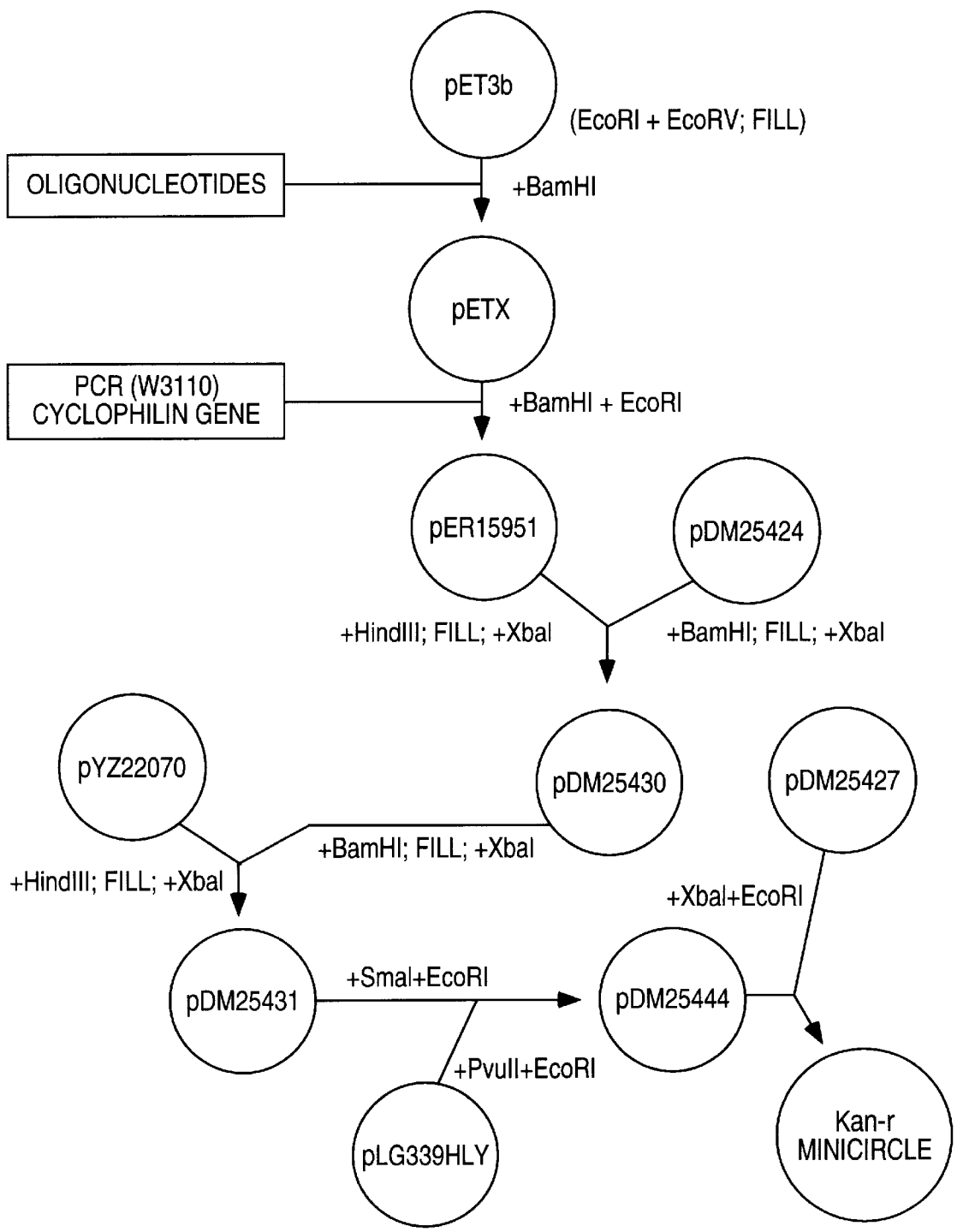

The general strategy for constructing a chromosomal transfer DNA (CTD) with the double cassette system is shown in FIG. 7. The strategy used to create the chromosomal transfer DNA carrying the DsbA::ubiquitin::IGF-I fusion gene is shown in FIG. 12. Following chromosomal integration, the fusion gene was expressed, resulting in extremely high levels of protein accumulation.

Figure 14:
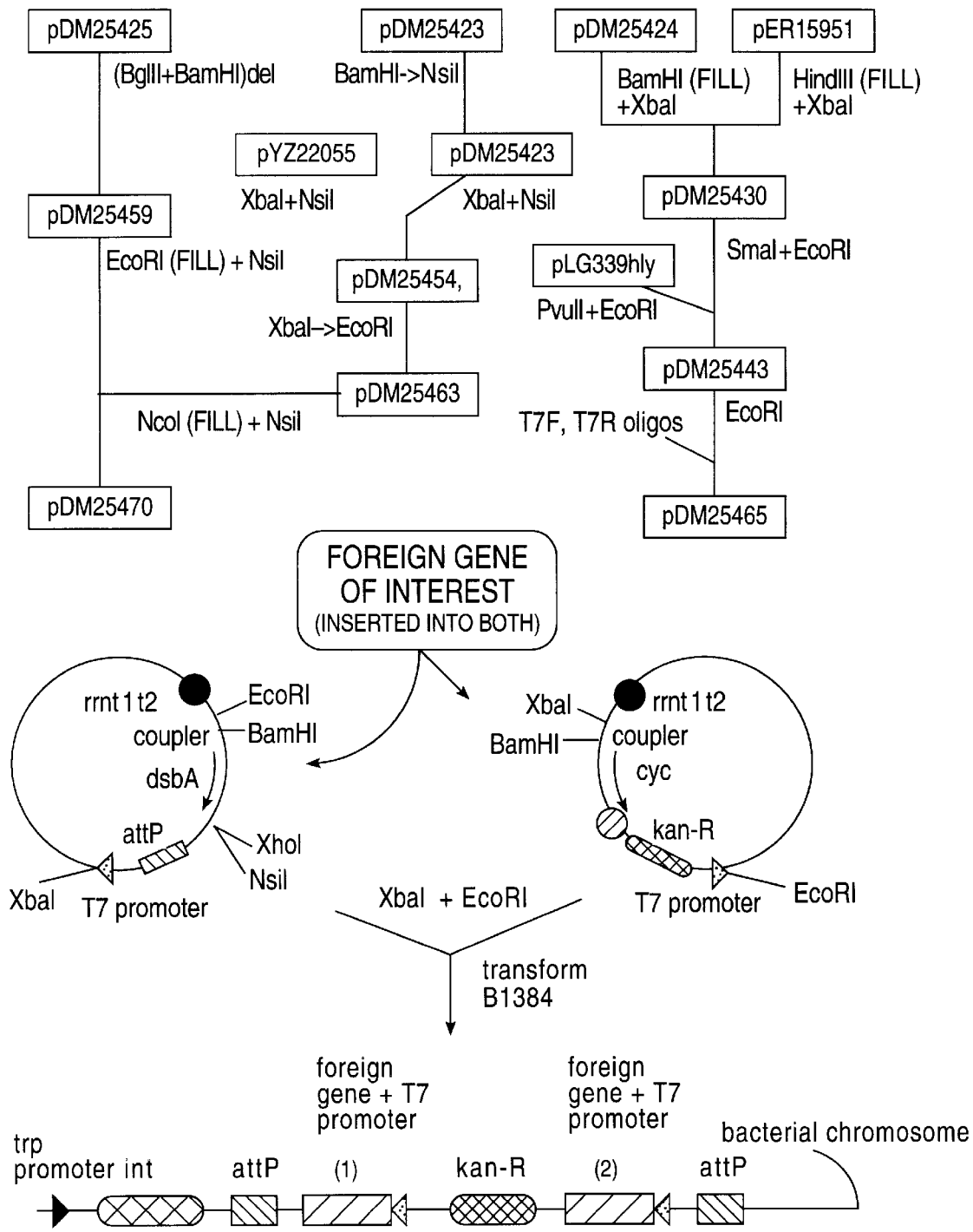
FIG. 14 shows the strategy for construction of the two DNA sources used in the double cassette system.
Figure 15:
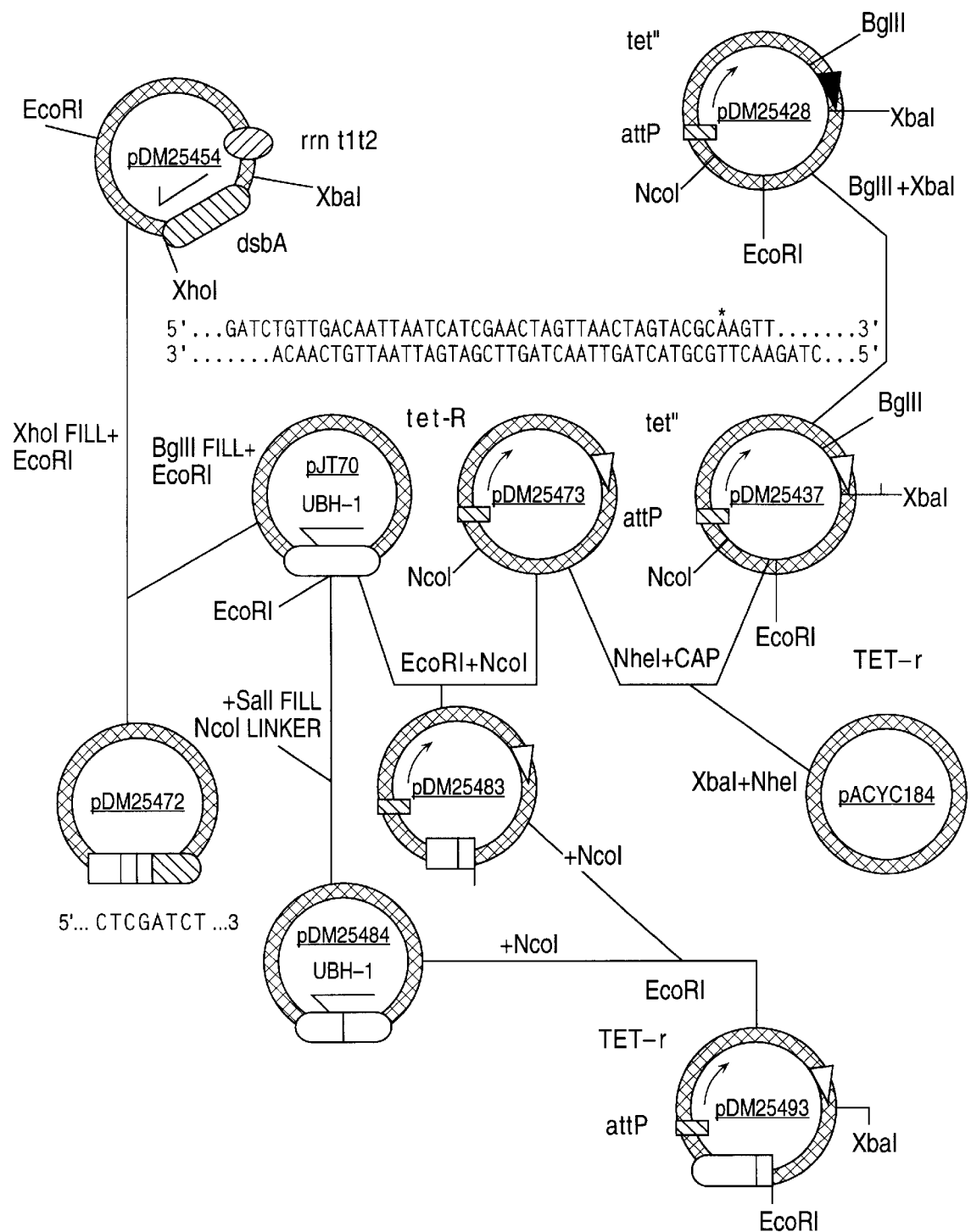
FIGS. 15 (SEQ ID NO:5 and SEQ ID NO:73) and 16 show the strategy used to construct chromosomal transfer DNAs for integration and expression of the yeast ubiquitin hydrolase gene.
Figure 16:
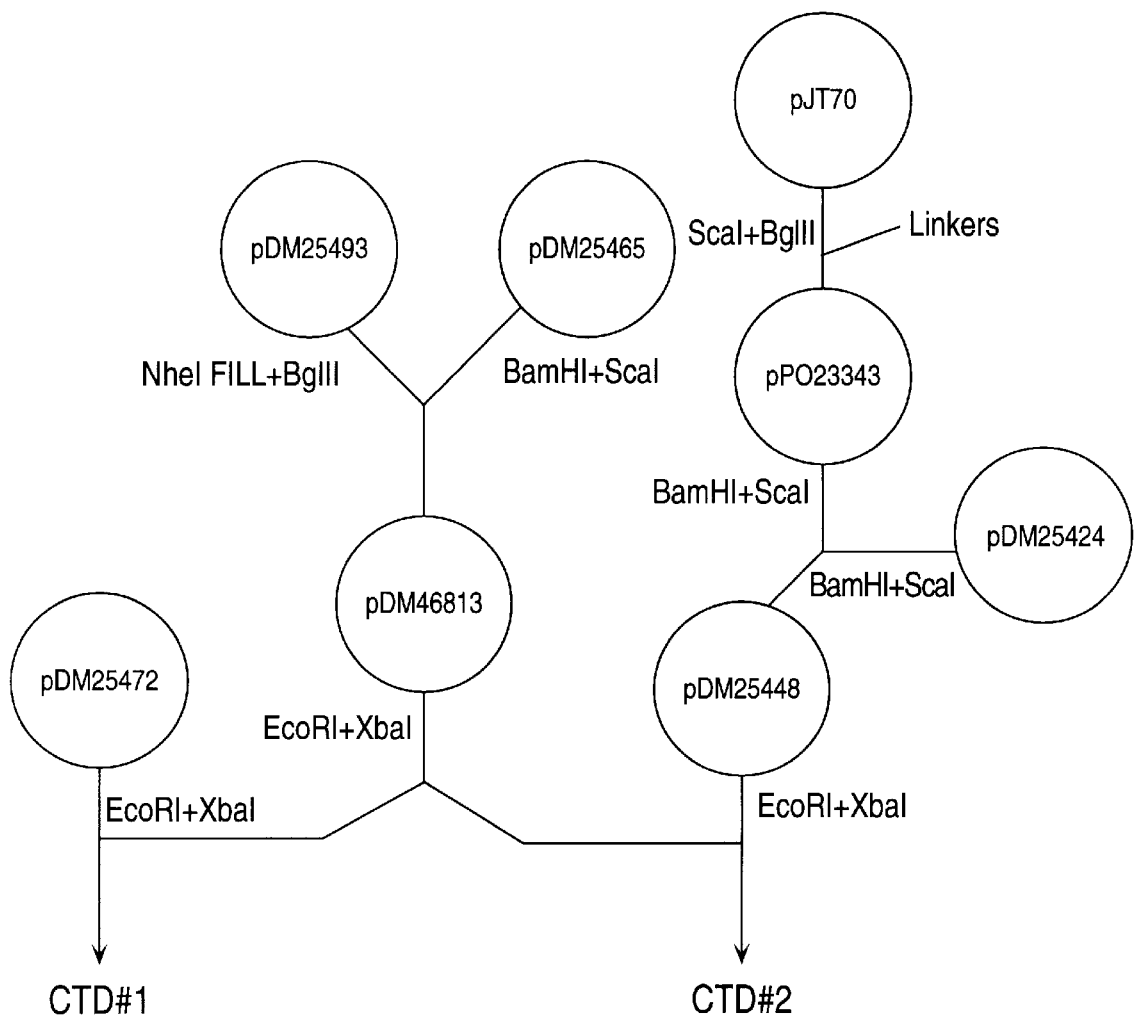

The double cassette binary system utilizes two plasmids, pDM25470 and pDM25465, as shown in FIGS. 7 and 14. pDM25425 is a pUC19 derivative carrying a copies of attP, the T7 promoter, and a copy of the rrntlt2 terminator, from which a 1.6 kb fragment was deleted by BglII/BamHI digestion. A terminator and a sequence encoding DsbA (a 1.5 kb NcoI(fill)/NsiI fragment from pDM25463) was added ligated to EcoRI(fill)/NsiI-digested pDM25459 to form pDM25470 (one of the double cassette binaries). The other double cassette plasmid, pDM25465, carries two copies of a terminator, a kanamycin resistance gene, and the cyclophilin gene (the use of the cyclophilin gene to aid in protein production is described in co-owned, co-pending U.S. patent application Ser. No. 08/101,506, incorporated herein by reference in its entirety). The cyclophilin gene was cloned from pER15951 (HinDIII(fill)/XbaI, 0.6 kb fragment) into pDM25424 (BamHI(fill)/XbaI, 5.2 kb fragment; a pUC19 backbone carrying two copies of a terminator and a kanamycin resistance gene). The kanamycin resistance gene in pDM25430 (derived from pDM25424) was insufficiently effective, so it was replaced with a kanamycin resistance gene from pLG339hly (PvuII/EcoRI digest), creating plasmid pDM25443. The T7 promoter was cloned into pDM25443 by annealing oligos T7F and T7R and ligating them the EcoRI-digested pDM25443, creating pDM25465.

Two sets of oligonucleotides were synthesized (1, 2, 1R, 2R and 3, 4, 3R, 4R), phosphorylated, denatured, and annealed. The annealing product of 1, 2, 1R, and 2R, which encodes ubiquitin, was ligated into pUC18 (SphI-BamHI digest). The annealing product of 3, 4, 3R, and 4R, which encodes IGF-I, was ligated into pUC18 (EcoRI-BamHI digest). The resulting plasmids were transformed into JM109 and the transformed host cells were selected on ampicillin plates. Transformants were analyzed for the presence of the ubiquitin and IGF-I sequences, then sequenced to identify correctly formed constructs. One isolate from each was selected, and designated pPO39354 and pPO39334, respectively.

```
5'-  CAG ATT TTC GTC AAG ACT TTG ACC GGT AAA ACC

ATA ACA TTG GAA GTT GAA CCT TCC GAT ACC ATC GAG

AAC GTT AAG GCG AAA ATT CAA GAC AAG GAA GGT ATC

CCT CCA GAT CA-3' (SEQ ID NO:10)
```

```
2
5'-  ACA AAG ATT GAT CTT TGC CGG CAA GCA GCT AGA

AGA CGG TAG AAC GCT GTC TGA TTA CAA CAT TCA GAA

GGA GTC CAC CTT ACA TCT TGT GCT AAG GCT CCG

CG-3' (SEQ ID NO:11)
```

```
1R
5'-  ATA CCT TCC TTG TCT TGA ATT TTC GCC TTA ACG

TTC TCG ATG GTA TCG GAA GGT TCA ACT TCC AAT GTT
```

-continued

ATG GTT TTA CCG GTC AAA GTC TTG ACG AAA ATC TGC

ATG-3' (SEQ ID NO:12)

2R
5'- GAT CCG CGG AGC CTT AGC ACA AGA TGT AAG GTG

GAC TCC TTC TGA ATG TTG TAA TCA GAC AGC GTT CTA

CCA TCT TCT AGC TGC TTG CCG GCA AAG ATC AAT CTT

TGT TGA TCT GGA GGG-3' (SEQ ID NO:13)

3
5'- GAT CCC CGC GGT GGT GGT CCG GAA ACC CTG TGC

GGT GCT GAA CTG GTT GAC GCT CTT CAG TTC GTT GCC

GGT GAC CGT GGT TTC TAC TTC AAC AAA CCG ACC GGT

TAC GGT TCC TCC TCC CGT CGT GCT CCG CAG-3' (SEQ ID NO:14)

4
5'- ACC GGT ATC GTT GAC GAA TGC TGC TTC CGG TCC

TGC GAC CTG CGT CGT CTG GAA ATG TAC TGC GCT CCG

CTG AAA CCG GCT AAA TCC GCT TAA TGC ATC GAT CTC

GAG-3' (SEQ ID NO:15)

3R
5'- AGC ACG ACG GGA GGA GGA ACC GTA ACC GGT CGG

TTT GTT GAA GTA GAA ACC ACG GTC ACC GCA AAC GAA

CTG AAG AGC GTC AAC CAG TTC AGC ACC GCA CAG GGT

TTC CGG ACC ACC ACC GCG GG-3' (SEQ ID NO:16)

4R
5'- AAT TCT CGA GAT CGA TGC ATT AAG CGG ATT TAG

CCG GTT TCA GCG GAG CGC AGT ACA TTT CCA GAC GAC

GCA GGT CGC AGG ACC GGA AGC AGC ATT CGT CAA CGA

TAC CGG TCT GCG G-3' (SEQ ID NO:17)

The ubiquitin and IGF-I sequences were isolated from pPO39354 and pPO39334 (by SphI-SacII and SacII-NsiI digests, respectively), and cloned into SphI-NsiI digested pDM25454 (a pUC19- based plasmid carrying a sequence coding for DsbA), to create a plasmid, desugnated pPO39358, containing a DsbA: :ubiquitin: : IGF-I fusion gene.

Figure 17:
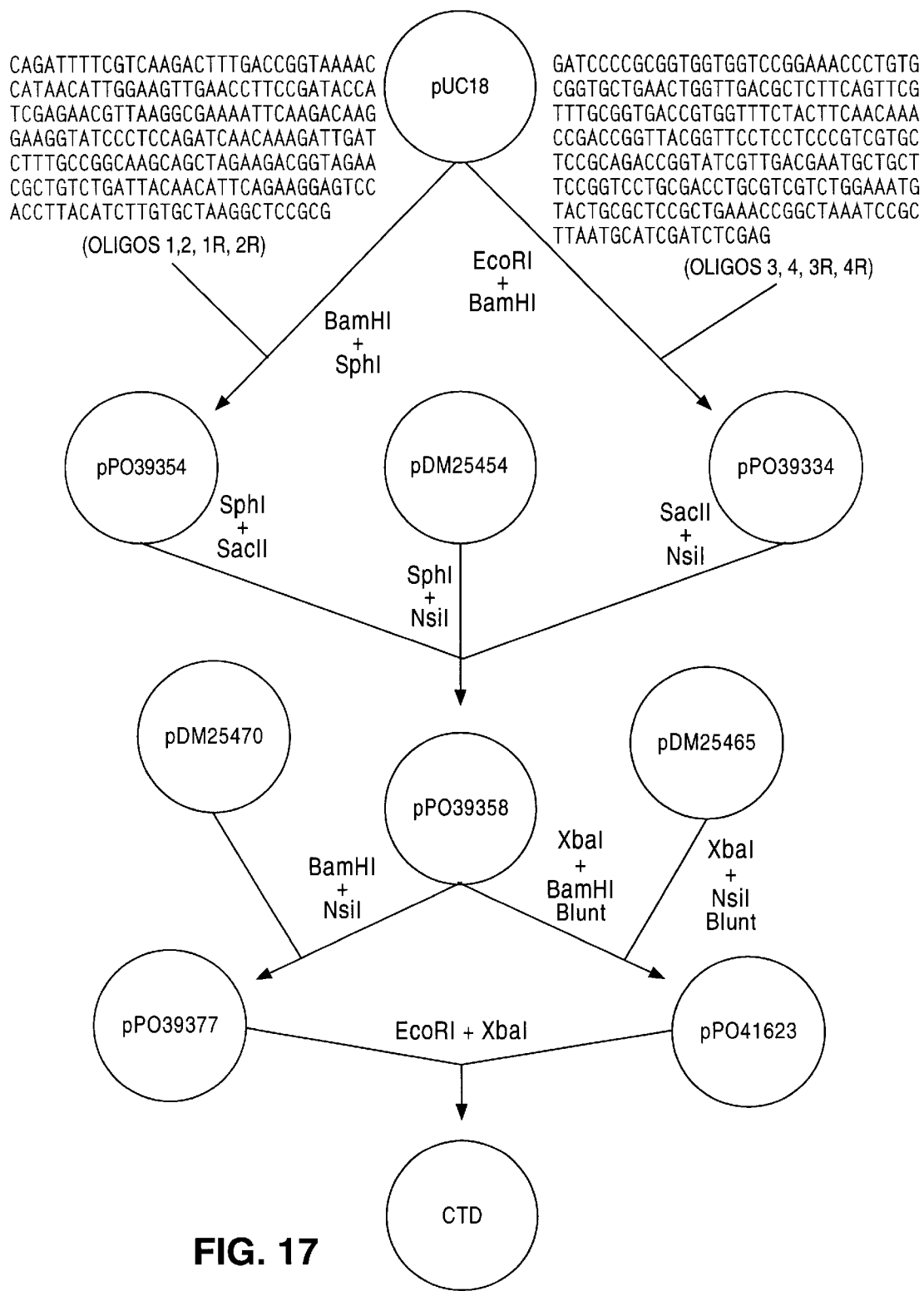
FIG. 17 (SEQ ID NO:T4 and SEQ ID NO:75) shows the strategy for constructing the chromosomal transfer DNA used to integrate and express a gene encoding a DsbA::ubiquitin::IGF-I fusion protein.

The fusion gene form pPO39358 was ligated into the double-cassette binary parent vectors pDM25470 and pDM2565 to create pPO393377 and pPO41623, respectively. EcoRI-XbaI fragments of pPO39377 and pPO41623 were ligated to form the chromosomal transfer DNA (FIG. 17).

The chromosomal transfer DNA was transformed into E. coli strain B1384, which contains an attP site as well as a sequence, under the control of the trp promoter, encoding the enzyme integrase (INT). Indole acrylic acid (1 mM) was added to induce the expression of INT and resulted in the integration of transduced chromosomal transfer DNA's. Cells were tested for chromosomal transfer DNA integration by:

Blue/yellow screening Cells were tested for integrated DNA by blue/yellow screening with AmpScreen (BRL). Colonies with a blue phenotype were further screened, yellow colonies were discarded.

PCR Cells were tested for properly integrated DNA by amplification of host cell chromosomal DNA using primer pairs:

T7F1    5'- AAT TGT CGA CAT TAA TAC GAC TCA CTA TAG

GGA GAC CAC AAC GGT TTC CCT GAA TTG TCG ACA TTA

ATA CGA CTC ACT ATA GGG AGA CCA CAA CGG TTT CCC

IGFREV   5'- CCC ATC GAT GCA TTA AGC GGA TTT AGC CGG TTT CAG-3' (SEQ ID NO:19)

which confirm the presence of the complete fusion gene with its promoter and

T7REV    5'- TGC TAG TTA TTG CTC AGC GG-3' (SEQ ID NO:20)

TRPBR2   5'- AAG GGC TTC ATC ATC GGT AAT AGA CA-3' (SEQ ID NO:21)

which confirm the integration of the chromosomal transfer DNA into the att site of B1384.

Production of protein from integrated genes requires T7 RNA polymerase activity, which is lacking in B1384. To test protein production from the integrated gene, P1 lysates were made using a B1384 integrant. The lysates were then transduced into *E. coli* strain W3110DE3 (as described in Example 1), which is Gal⁺ and carries a copy of the T7 RNA polymerase gene under the control of the lac promoter. Transductants were selected by plating on galactose minimal medium plates which contained 10 μg/ml kanamycin. Single kanʳGal⁺ colonies were isolated and reselected on galactose minimal medium plates with kanamycin. Kanʳ/Gal⁺ colonies were further analyzed by PCR using primer pairs:

isolates against phage 4107, which requires T7 RNA polymerase activity to lyse bacteria (Novagen). An isolate which contained an intact fusion gene expression cassette and which was positive for T7 RNA polymerase activity, designated c49222, was used to test protein production. Protein expression was induced by the addition of IPTG to the a culture of c49222 for two hours. Protein production was analyzed by SDS-PAGE of a whole cell lysate on a 12.5% a acrylamide gel. Densitometric analysis of and SDS-PAGE gel showed that the DsbA::ubiquitin::IGF-I fusion protein accumulated to 22.3% of total cell protein.

ATT3     5'- GAG GTA CCA GCG CGG TTT GAT CAG-3' (SEQ ID NO:22)

T7RNAP1  5'- CAG CGT TAT CCG CAA CCT CAC C-3' (SEQ ID NO:23)

which showed that the upstream att site flanking the prophage in W3110DE3 is unoccupied; and T7F1     5'- AAT TGT CGA CAT TAA TAC GAC TCA CTA TAG GGA GAC CAC AAC GGT TTC CCT GAA TTG TCG ACA TTA ATA CGA CTC ACT ATA GGG AGA CCA CAA CGG TTT CCC TG-3' (SEQ ID NO:24)

IGFREV   5'- CCC ATC GAT GCA TTA AGC GGA TTT AGC CGG TTT CAG-3' (SEQ ID NO:25)

which confirmed that the fusion gene expression cassette was transferred intact.

Individual isolates from the W3110DE3 transduction were tested for T7 RNA polymerase activity by streaking the P1 lysates were also used to transduce the integrated gene into *E. coli* strain cDM46809 (which is camʳ, malE deleted, and contains an attB site introduced into the lac region). Transductants were selected by growth on plates containing kanamycin and chloramphenicol. Integration into the lac region was confirmed by PCR using primer pair:

UBI1  5'- CAG ATT TTC GTC AAG ACT TTG ACC GGT AAA

ACC ATA ACA TTG GAA GTT GAA CCT TCC GAT ACC ATC

GAG AAC GTT AAG GCG AAA ATT CAA GAC AAG GAA GGT

ATC CCT CCA GAT CA -3' (SEQ ID NO:26)

1224  5'- CGC CAG GGT TTT CCC AGT CAC GAC -3' (SEQ ID NO:27)

A P1 lysate was then made from an isolate which was kan$^r$/cam$^r$ and integrated into the lac region. This P1 was used to transduce W3110DE3. Transductants were selected for kanamycin and chloramphenicol resistance by growth on selective media. Kan$^r$/cam$^r$ isolates were tested for T7 RNA polymerase activity by streaking against phage 4107 as described above. Two isolates positive for T7 RNA polymerase activity, designated c49258#46 and c49258#50, were tested for protein accumulation by induction with IPTG for two hours. Whole cell lysates were analyzed by SDS-PAGE using 12.5% acrylamide gels. DsbA::ubiquitin::IGF-I fusion protein accumulated to 19.6% of total cell protein in c49258#46, as measured by densitometry of an SDS-PAGE gel.

Figure 24:
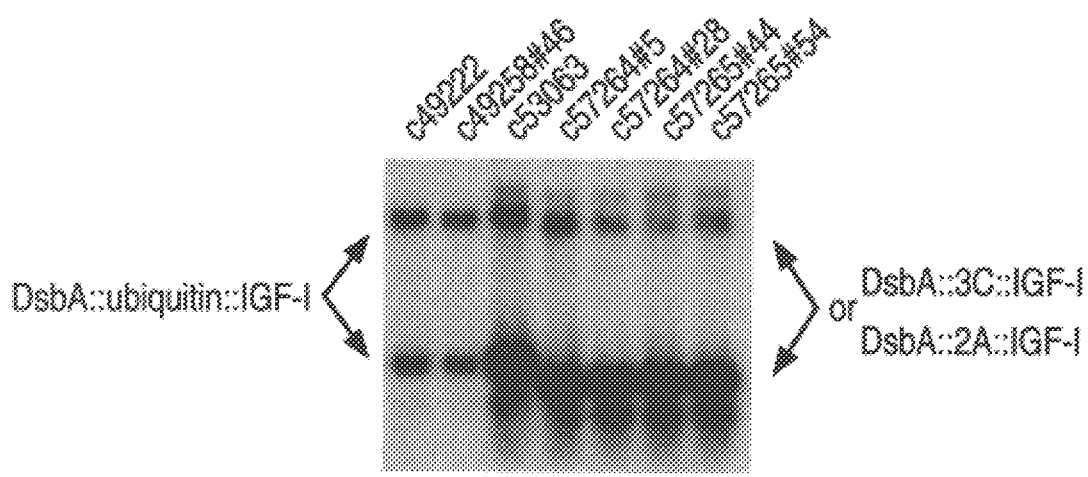
FIG. 24 shows a Southern blot of chromosomal DNA isolated from c49222, c49258#46, c53063, c57264#5, c57264#28, c57265#44, and c57265#54. The blot was probed with a DNA fragment encoding ubiquitin fused to IGF-I. The higher molecular weight band in each lane represents a single copy of the integrated IGF-I fusion protein gene in each isolate. The lower molecular weight band also represents the integrated IGF-I fusion protein gene, but this fragment can be amplified by chromosomal amplification. Isolates c53063, c57264#5, c57264#28, c57265#44, and c57265#54 have clearly been amplified, showing about 3 to 5 fold amplification.

Southern blot analysis of chromosomal DNA from c49222 and c49258#46 was performed to check the copy number of the integrated DNA. Chromosomal DNA from c49222 and c49258#46 was isolated, digested with restriction endonucleases, transferred to Hybond-N (Amersham), and probed with the a DNA fragment encoding the ubiquitin and IGF-I portions of the fusion protein. Analysis of the Southern blot showed that there were approximately two copies each of the DsbA::ubiquitin::IGF-I gene integrated into the chromosomes c49222 and c49258#46 (FIG. 24), i.e. a single copy of the integrated DNA). This result was surprising and unexpected in view of the levels of accumulation of DsbA::ubiquitin::IGF-I protein shown by SDS-PAGE (22.3% and 19.6% of total cell protein, respectively). Ordinarily, it is expected that such high levels of protein accumulation can only be accomplished by expression of heterologous genes carried by high copy number plasmids.

DsbA::ubiquitin::IGF-I was also produced by integrating a chromosomal transfer DNA carrying a gene for tetracycline resistance in addition to the gene for kanamycin resistance. P1 lysates prepared from a B1384 integrant were used to transduce W3110DE3 to kanamycin resistance (see Example 1). Kanr isolates were checked for properly integrated DNA using primer pairs T7F1×IGFREV and ATT3× T7RNAP1 as described above. Isolates were also tested for T7 RNA polymerase activity by streaking against phage 4107 as described above. Isolates positive for T7 RNA polymerase activity were then selected for amplification of the integrated DNA by growth on medium containing kanamycin (10 µg/ml) and tetracycline (30µg/ml). The tetracycline allele incorporated into this construct is effective at high copy number, therefore colonies which are tetracycline resistant may have amplified the integrated DNA. Kan$^r$/tet$^r$ colonies were tested for protein accumulation by induction with IPTG, as described above. All kan$^r$/tet$^r$ colonies produced the fusion protein upon induction.

Example 3

Chromosomal expression of ubipuitin hydrolase (UBP-1)

The construction of plasmids used in this example is described in FIGS. 10-16. pJT70 was the source of the ubiquitin hydrolase. pDM25493 was the source of the trp promoter used for this construct. chromosomal transfer DNA's for the yeast UBP-1 gene under the control of the trp promoter were prepared from pDM46813 and either pDM25472 or pDM25448. In this example, pDM25472 was used (i.e. chromosomal transfer DNA#1 of FIG. 16). The fusion gene formed by this chromosomal transfer DNA encodes an in-frame fusion between a truncated DsbA gene and a UBP-1 cDNA missing the amino-terminal 92 codons.

The chromosomal transfer DNA was introduced into B1384 as in Example 2. Integrants were selected for with kanamycin (10 µg/ml). Isolated colonies were tested in a diagnostic PCR reaction using primers TRPPF and 1239 (as described in Example 1). All isolates were positive by this test. All isolates were also ampicillin sensitive.

One colony was selected for further characterization. P1 lysates were prepared of this isolate and used to transduce W3110DE3 to kanamycin resistance as described in Example 1. Kanamycin resistant colonies were further tested by PCR using primers ATT3 and T7RNAP1, as described in Example 2. All isolates showed the expected location at the attB/P or attP/B sites flanking the DE3 lysogen.

The isolates were tested for protein expression by testing for ubiquitin hydrolase activity. Isolates were grown in casamino acid minimal medium, harvested and lysed by sonication. The soluble fraction was assayed for activity by incubation with DsbA::ubiquitin::IGF-I fusion protein substrate at 370 C for one hour. Cleavage was monitored by SDS-PAGE. All isolates (WBD311, 312, 313, 314, 331, and 332) showed good levels of enzyme activity (i.e. complete cleavage of the substrate under assay conditions).

Example 4

Figure 18:
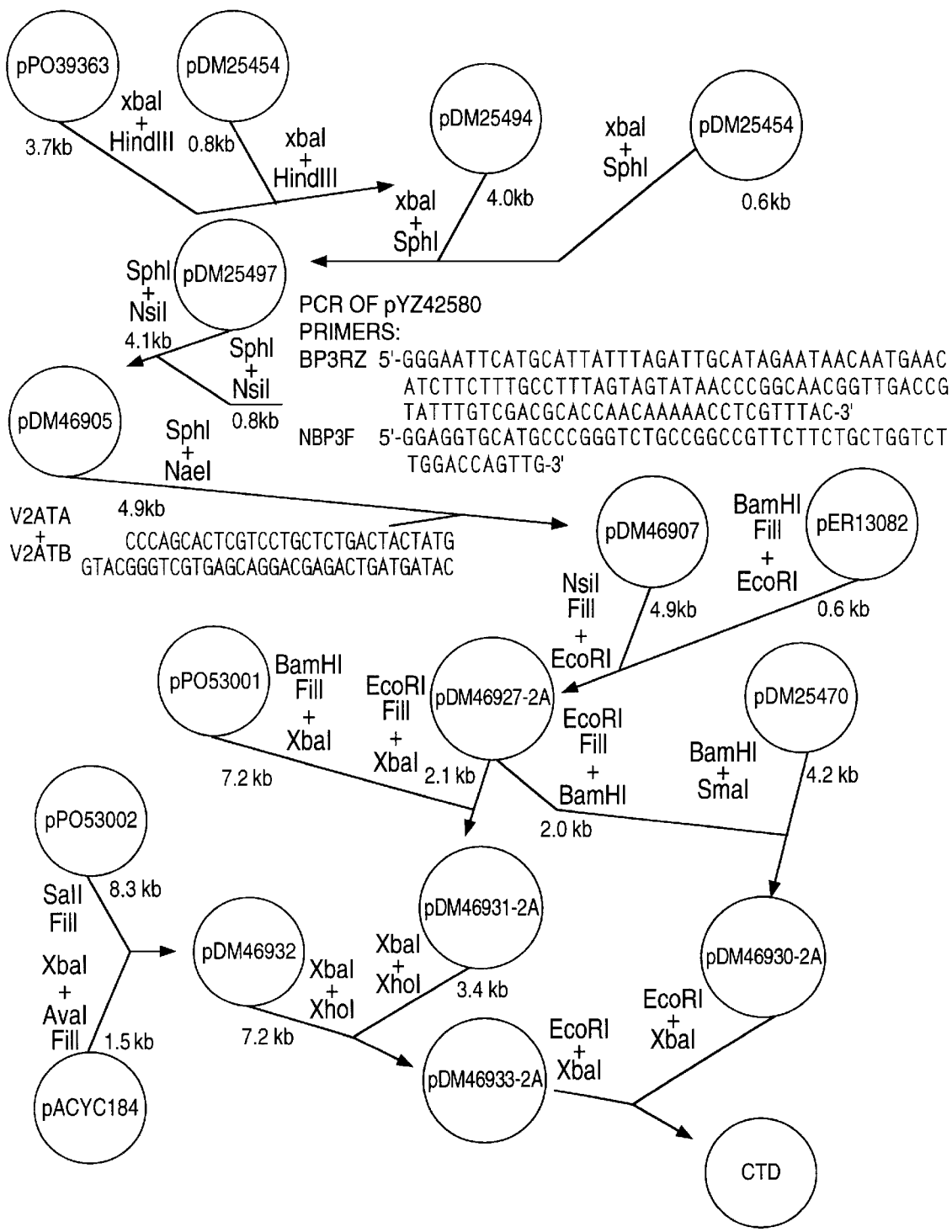
FIG. 18 (SEQ ID NO:76 through SEQ ID NO:79) shows the strategy for constructing the chromosomal transfer DNA used to integrate and express a gene encoding a DsbA::2A::IGFBP-3 fusion protein.

Expression of an insulin-like qrowth factor binding protein-3 (IGFBP-3) fusion protein A chromosomal transfer DNA carrying a fusion protein comprising DsbA, a linker including a human rhinovirus 2A protease site, and IGFBP-3 (DsbA::2A::IGFBP-3) was created using the double cassette method. Construction of the fusion gene and chromosomal transfer DNA are shown in FIG. 18. DsbA was from pDM46905, the 2A protease site was created by annealing primers V2ATA and V2ATB, and IGFBP-3 was PCR amplified from pYZ42580 using primers BP3RZ and NBP3F.

The IGFBP-3 gene used to create the DsbA::2A::IGFBP-3 fusion was created by annealing and ligating a number of synthetic oligonucleotides, which, when fully assembled, code for IGFBP-3 protein. The oligonucleotides were assembled in three segments; 5', F1-1  5'-AGC TTG GTG CTT CTT CTG CTG GTC TTG GAC CAG TTG TTC GTT GTG AAC CAT GTG ATG CAC GAG CTT TAG CTC AAT GTG CTC CAC CAC CAG CTG TT-3'(SEQ ID NO:28), F1-2  5'-TGT GCT GAA TTA GTT CGA GAA CCA GGT TGT GGT TGT TGT TTA ACT TGT GCT TTA TCT GAA GGT CAA CCA TGT GGT ATT TAT ACT GAA CGT TGC GG-3'(SEQ ID NO:29), F1-3  5'-TAG TGG TTT GCG TTG TCA ACC AAG CCC AGA TGA AGC TAG GCC TTT ACA AGC ATT ATT AGA TGG TCG AGG TCT GTG TGT TAA TGC GTC CGC TGT TTC TCG ATT GCG CGC G-3'(SEQ ID NO:30), C1-1  5'-TCG ACG CGC GCA ATC GAG AAA CAG CGG ACG CAT TAA CAC ACA GAC CTC GAC CAT CTA ATA ATG CTT GTA AAG GCC TAG CTT CAT CTG GGC TTG GTT G-3'(SEQ ID NO:31), C1-2  5'-ACA ACG CAA ACC ACT ACC GCA ACG TTC AGT ATA AAT ACC ACA TGG TTG ACC TTC AGA TAA AGC ACA AGT TAA ACA ACA ACC ACA ACC TGG TTC TC-3'(SEQ ID NO:32), and C1-3  5'-GAA CTA ATT CAG CAC AAA CAG CTG GTG GTG GAG CAC ATT GAG CTA AAG CTC GTG CAT CAC ATG GTT CAC AAC GAA CAA CTG GTC AAG ACG CAG CAG AAG AAG CAC C-3'(SEQ ID NO:33)

were annealed and ligated to form the 5' segment of the IGFBP-3, then cloned into pUC18 (HinDIII-SalI digest); this construct was designated pYZ37437. The 3' section of the gene was created by annealing and ligating oligonucleotides F-1  5'-TCG ACG TGA GAT GGA GGA TAC CTT AAA CCA TTT AAA ATT TTT GAA CGT TTT ATC CCC GCG TGG CGT TCA TAT CCC GAA TTG CGA T-3'(SEQ ID NO:34), F-2  5'AAA AAA GGC TTC TAC AAA AAG AAA CAA TGC CGT CCG AGT AAG GGT CGT AAA CGA GGT TTT TGT TGG TGC GTT GAC AAA TAC GGT-3'(SEQ ID NO:35), F-3  5'-CAA CCG TTG CCG GGT TAT ACT ACT AAA GGC AAA GAA GAT GTT CAT TGT TAT TCT ATG CAA TCT AAA TAA TGC ATC TCG AG-3'(SEQ ID NO:36), C-1  5'-AAT TCT CGA GAT GCA TTA TTT AGA TTG CAT AGA ATA ACA ATG AAC ATC TTC TTT GCC TTT AGT AGT ATA ACC CGG C-3'(SEQ ID NO:37), C-2  5'-AAC GGT TGA CCG TAT TTG TCA ACG CAC CAA CAA AAA CCT CGT TTA CGA CCC TTA CTC GGA CGG CAT TGT TTC TTT TTG TAG AAG-3'(SEQ ID NO:38), and C-3  5'-CCT TTT TTA TCG CAA TTC GGG ATA TGA ACG CCA CGC GGG GAT AAA ACG TTC AAA AAT TTT AAA TGG TTT AAG GTA TCC TCC ATC TCA CG-3'(SEQ ID NO:39), followed by cloning into SalI-EcoRI digested pUC18 (designated pYZ37405). pYZ374100 contained the middle segment of the IGFBP-3 gene and was created by annealing and ligating oligonucleotides MF1  5'-CGC GCT TAT TTA TTA CCT GCC CCA CCG GCA CCG GGT AAC GCC TCC GAA A-3'(SEQ ID NO:40), MF2  5'-GCG AAG AGG ATC GTT CTG CGG GTT CCG TTG AAT CTC CAA GTG TGA GTT CTA CCC ATC GAG TTA GCG ACC CGA AA-3'(SEQ ID NO:41), MF3  5'-TTT CAT CCG TTG CAC TCT AAA ATC ATT ATT ATT AAA AAG GGT CAC GCA AAG GAT TCT CAA CGT TAT AAG GT-3'(SEQ ID NO:42), -continued MF4 5'-GGA TTA TGA AAG CCA ATC TAC CGA CAC TCA AAA TTT TAG TAG TGA AAG TAA ACG TGA AAC CGA GTA CGG CCC GTG-3'(SEQ ID NO:43), MB1 5'-TCG ACA CGG GCC GTA CTC GGT TTC ACG TTT ACT TTC ACT ACT AA-3'(SEQ ID NO:44), MB2 5'-AAT TTT GAG TGT CGG TAG ATT GGC TTT CAT AAT CCA CCT TAT AAC GTT GAG AAT CCT TTG CGT GAC CCT TTT T-3'(SEQ ID NO:45), MB3 5'-AAT AAT AAT GAT TTT AGA GTG CAA CGG ATG AAA TTT CGG GTC GCT AAC TCG ATG GGT AGA ACT CAC ACT TGG AGA TT-3'(SEQ ID NO:46), and MB4 5'-CAA CGG AAC CCG CAG AAC GAT CCT CTT CGC TTT CGG AGG CGT TAC CCG GTG CCG GTG GGG CAG GTA ATA AAT AAG-3'(SEQ ID NO:47), digesting the ligated DNA with BssHII and SalI, end filling with Klenow then cloning into Klenow-filled, XbaI-digested pUC18.

PCR amplification of a segment of pYZ37490 was used to add a SacII site and repair a cloning artifact.

Primer pairs pF1 5'-GGT TGT TGT TTA ACT TGT GCT TTA TCT GAA GGT CAA CCA TGT GGT ATT TAT ACT GAA CGT TGC GGT AGT GGT TTG CGT TGT CAA CCA AGC CCA GAT GAA GCT AGG-3'(SEQ ID NO:48)

1233 5'-AGC GGA TAA CAA TTT CAC ACA GGA-3'(SEQ ID NO:49)

and pR1 5'-TAA AGC ACA AGT TAA ACA ACA ACC ACA ACC TGG TTC TCG AAC TAA TTC AGC ACA AAC AGC TGG TGG TGG AGC ACA TTG AGC TAA AGC TCG TGC ATC ACA TGG T-3'(SEQ ID NO:50)

1224 5'-CGC CAG GGT TTT CCC AGT CAC GAC-3'(SEQ ID NO:51)

were used to introduce the restriction site and repair the defect. The two PCR amplified fragments were then mixed and amplified to form a single DNA using primer pair 1233×1224. The resulting DNA segment was cloned into HinDIII-SalI digested pYZ37437, creating pYZ37490.

PCR amplification was also used to introduce an additional SacII site, to facilitate later cloning steps.

Primers

5pMP 5'- GAC TGC AAG CTT CCG CGG TGG TGG TGC TTC TTC TGC TGG TCT TGG A-3'(SEQ ID NO:52)

and 1233 5'-AGC GGA TAA CAA TTT CAC ACA GGA-3'(SEQ ID NO:49)

were used to amplify a segment of pYZ37490, which was then ligated into HinDIII-SalI digested pYZ37490, forming pYZ42519.

The IGFBP-3 gene was assembled from the three segments in a three-way ligation reaction. pYZ42519 (HinDIII-BssHII digest), pYZ374100 (BssHII-SalI digest) and pYZ37405 (SalI-EcoRI digest) were ligated into HinDIII-EcoRI digested pUC18. A properly assembled clone was identified by restriction mapping and sequencing.

Cloning artifacts were repaired using PCR. BPFIX1 was created by amplifying pYZ42509 with primers YZM1  5'  -CTC  GAT  TGC  GCG  CTT  ATT  TAT  TAC  C-3'(SEQ ID NO:53)
and YZM2  5'  -TCT  CAC  GTC  GAC  ACG  GGC  CGT  ACT  CGG
TTT  CAC  GTT  TAC  TCA  GTA  CTA  AAA  T-3'(SEQ ID NO:54), and cloning the resulting fragment (BssHII-SalI digested) into a BssHII-SalI digest of pYZ42509. A HinDIII-BssHII digest of BPFIX1 was ligated with a HinDIII-BssHII digest of pYZ42519 to create pYZ42529. A second repair was made using primer pairs

715F1'  5'  -TGT  TGG  TGC  GTC  GAC  AAA  TAC  GGT  C-3'(SEQ ID NO:55)

1233  5'  -AGC  GGA  TAA  CAA  TTT  CAC  ACA  GGA-3'(SEQ ID NO:56)
and

715R'  5'  -GAC  CGT  ATT  TGT  CGA  CGC  ACC  AAC  A-3'(SEQ ID NO:57)

1224  5'  -CGC  CAG  GGT  TTT  CCC  AGT  CAC  GAC-3'(SEQ ID NO:58)

This repaired a cloning defect and added a SalI site. Two DNA fragments were amplified from pYZ42529 using primer pairs 715F1'×1233 and 715R'×1224. These two fragments were mixed and PCR amplified into a single DNA fragment using 1233×1224. This single fragment was digested with BssHI and SalI, then ligated into a BssHI-SalI digest of pYZ42529, creating pYZ50559.

pYZ42580, the donor construct for the IGFBP-3 gene, was created by ligation of EcoRI-SacII fragments from pYZ50559 and pDM25497.

The chromosomal transfer DNA carrying the DsbA::2A::IGFBP-3 fusion gene were transfected into *E. coli* strain B1384, which was grown in the presence of 100 μM IAA to induce the expression of INT and the integration of the chromosomal transfer DNA. Integrants were selected with kanamycin. All isolates were also ampicillin sensitive.

Isolates were further characterized by diagnostic PCR amplification of the host cell chromosome. PCR amplification with primer pairs 1227  5'  -TAA  TAC  GAC  TCA  CTA  TAG  GGA  GA-3'(SEQ ID NO:59)

BP3-607 5'  -GGG  ATA  TGA  ACG  CCA  CGC  GGG  GAT  AA-3'(SEQ ID NO:60),

INT107 5'  -GCG  GAG  AAA  CCA  TAA  TTG  CAT  CTA  CTC-3'(SEQ ID NO:61),

BP3-559 5'  -CGT  GAA  ACC  GAG  TAC  GGC  CCG  TGT  C-3(SEQ ID NO:62),
and

T7REV  5'  -TGC  TAG  TTA  TTG  CTC  AGC  GG-3'(SEQ ID NO:63)

TRPBR2 5'  -AAG  GGC  TTC  ATC  ATC  GGT  AAT  AGA  CA-3'(SEQ ID NO:64)

confirmed the proper integration of the intact chromosomal transfer DNA into the chromosome at the att site.

Figure 25A:
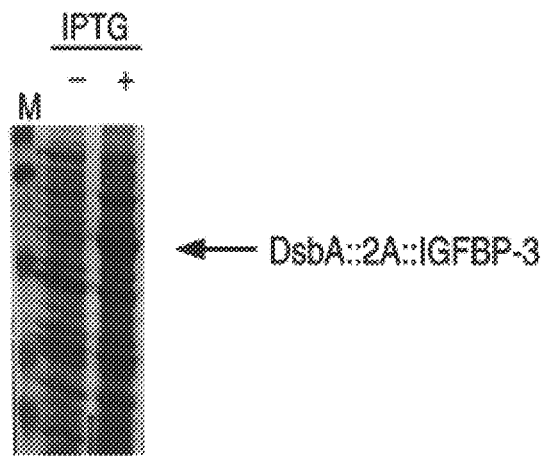
FIG. 25 shows coomassie blue-stained SDS-PAGE gels showing protein accumulation in isolates carrying integrated genes encoding IGFBP-3 fusion proteins. A) shows protein accumulation in an isolate expressing a DsbA::2A::IGFBP-3 fusion protein. The right lane shows protein expression after induction of T7 RNA polymerase by addition of IPTG to the culture medium. B) shows protein accumulation in an isolate expressing a DsbA::3C::IGFBP-3 fusion protein. As in FIG. 23, the bands representing the fusion protein are easily visible. Densitometric scanning of these gels found that the accumulated protein represented 22.6% in Panel A, and the two isolates in Panel B accumulated 33.% and 28.2% of total cell protein (eft to right, respectively).
Figure 25B:
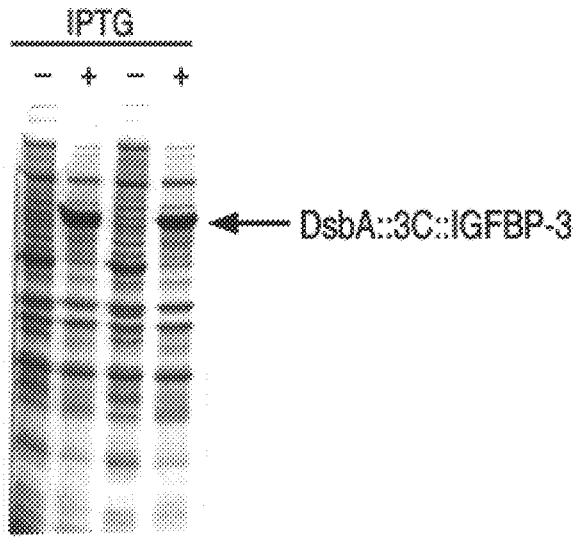

P1 lysates were prepared from a single isolate and used to transduce W3110DE3 to kanamycin resistance (as described in Example 1). Kanamycin resistant isolates were assayed for T7 RNA polymerase activity by streaking against phage 4107, as described in Example 2. Isolates with T7 RNA polymerase activity were then tested for expression of the fusion gene by induction with IPTG, followed by analysis of protein expression by SDS-PAGE of whole cell lysates on 12.5% polyacrylamide gels. Densitometric analysis of whole cell lysates indicated that the DsbA::2A::IGFBP-3 fusion protein accumulated to a level of 22.6% (FIG. 25 A).

Example 5

Production IGF-I fusion proteins

Figure 19:
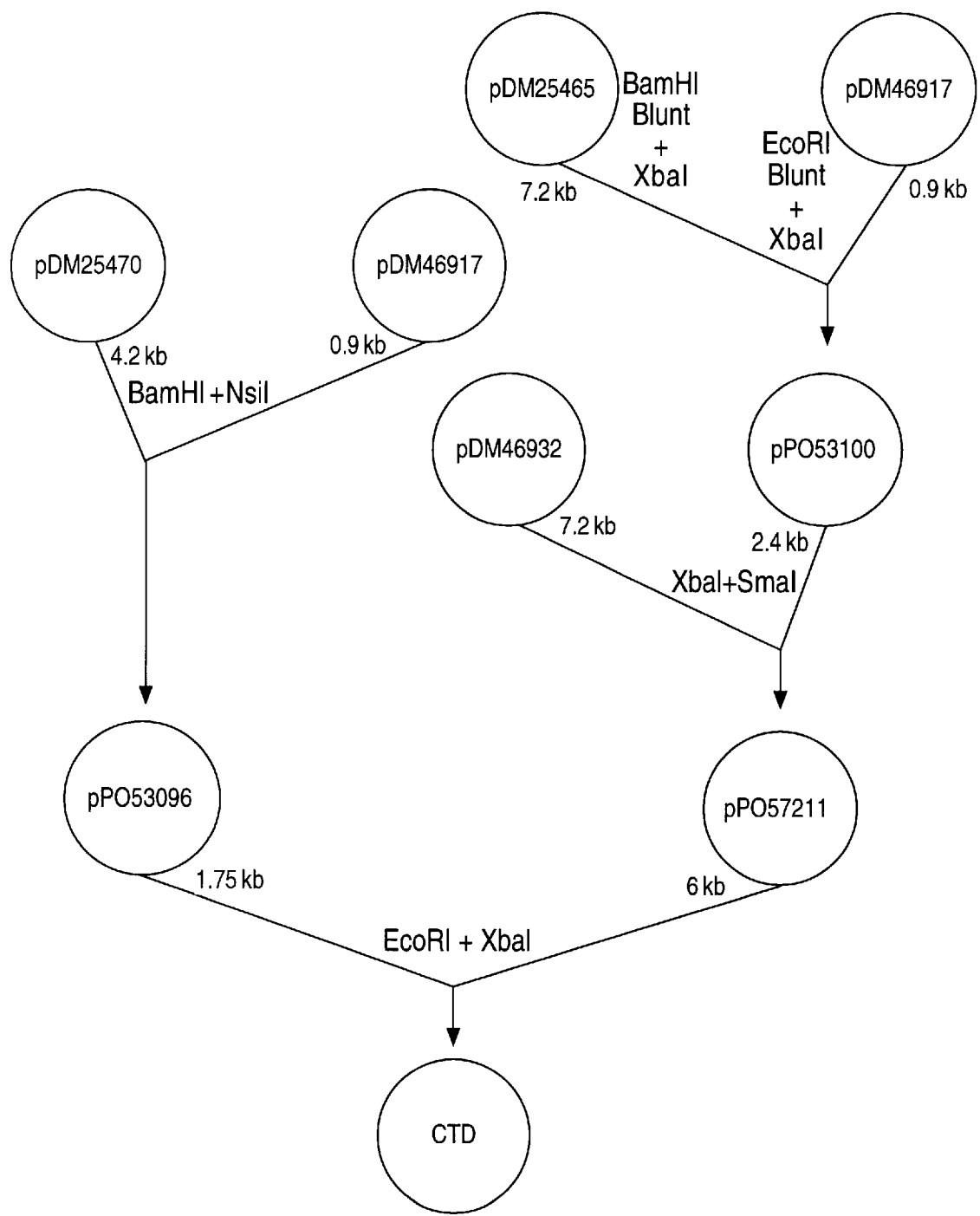
FIGS. 19 and 20 show the strategies used to construct chromosomal transfer DNAs used to integrate and express genes coding for DsbA::2A::IGF-I (FIG. 19) and DsbA::3C::IGF-I (FIG. 20) fusion proteins.
Figure 20:
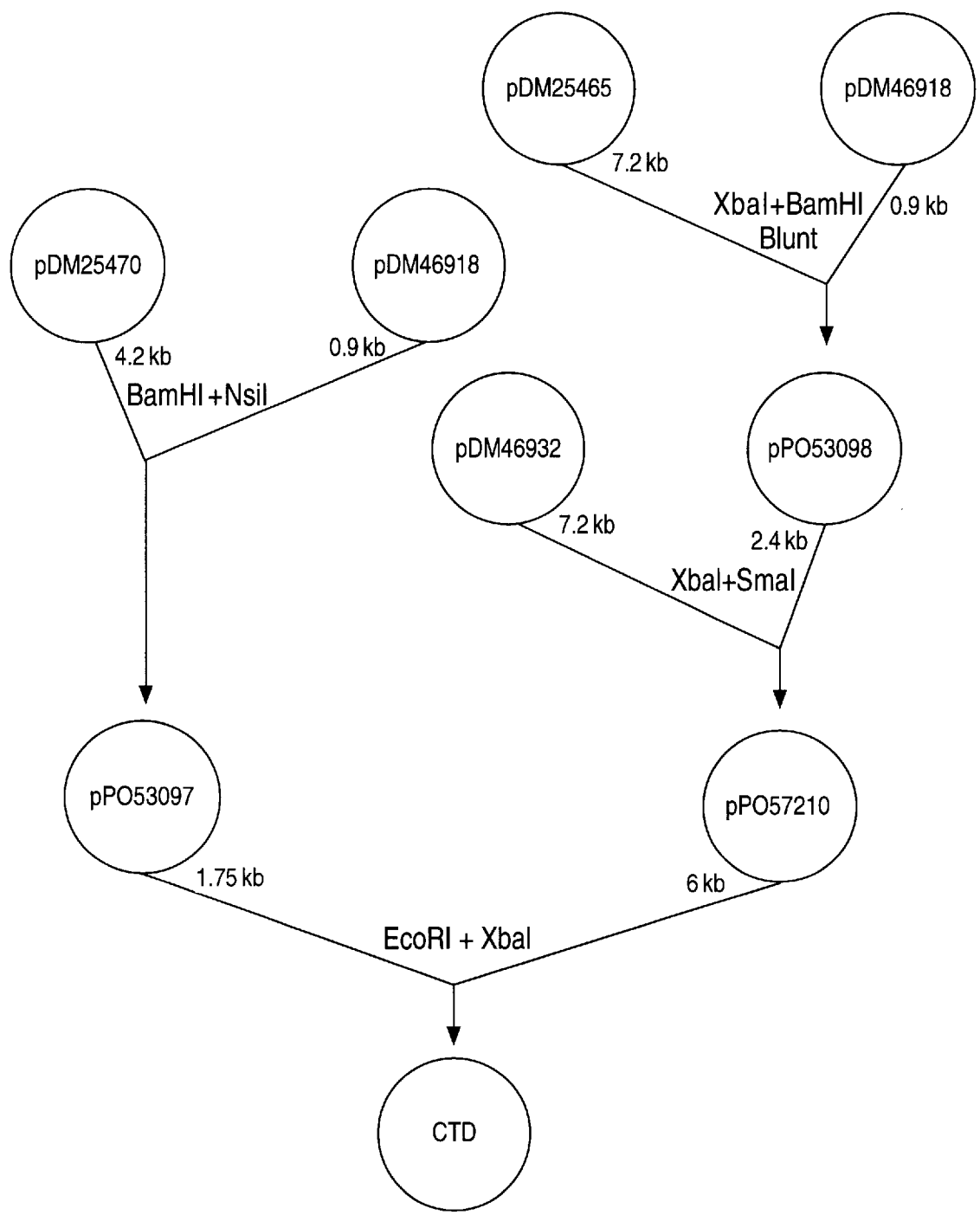

Fusion proteins including DsbA and IGF-I linked by a sequence including a site for either human rhinovirus 2A or 3C protease were produced using the double cassette binary system. Construction of binary plasmids and chromosomal transfer DNAs is diagramed in FIGS. 19 and 20.

For expression of DsbA::2A::IGF-I, EcoRI/XbaI digest fragments of pPO53096 and pPO57211 were ligated to form the chromosomal transfer DNA (CTD-DsbA::2A::IGF-I). EcoRI/XbaI fragments of pPO53097 and pPO57210 were ligated to form a chromosomal transfer DNA carrying a gene encoding DsbA::3C::IGF-I (CTD-DsbA::3C::IGF-I). CTD-DsbA::3C::IGF-I and CTD-DsbA::2A::IGF-I were each transformed into B1384 cells in the presence of indole acrylic acid (to induce INT expression). Transformants were grown on media containing kanamycin to select for integrants. Nine individual kan$^r$ colonies from each transformation were tested for ampicillin sensitivity. All tested colonies were ampicillin sensitive.

Isolates were tested for correctly integrated DNA by PCR amplification with primer pairs T7F1×IGFREV and T7REV×TRPBR2 to confirm the presence of the intact fusion gene and integration into the att site of B1384, as described in Example 2.

P1 lysates were prepared from one of the B1384 integrants from each transformation and used to transduce W3110DE3 to kanamycin resistance. Kan$^r$/gal$^+$isolates were tested for the presence of T7 RNA polymerase activity as described in Example 2. Isolates positive for T7 RNA polymerase activity were further tested by PCR using primer pairs T7F1×IGFREV and ATT3×T7RNAP1 to confirm appropriate integration of the intact fusion gene, as described in Example 2.

Two isolates from each transduction (c57265#44 and c57265#54 for DsbA::2A::IGF-I; c57264#5 and c57264#28 for DsbA::3C::IGF-I) were then grown on medium containing both kanamycin and tetracycline. Both DsbA::3C::IGF-I and CTD-DsbA::2A::IGF-I carry a tetracycline resistance allele which confers resistance when the gene is in high copy number. Growth in the presence of tetracycline selects for amplification of the integrated DNA. Both isolates from each transduction were kan$^r$/tet$^r$. The isolates were then tested for expression of the fusion proteins by induction with IPTG. Protein expression was assayed by SDS-PAGE of whole cell lysates. Densitometric scanning of a SDS-PAGE gel showed that the two isolates expressing DsbA::3C::IGF-I fusion protein accumulated the fusion protein to 20% and 20.1% of total cell protein and the two isolates expressing DsbA::2A::IGF-I accumulated the fusion protein to 25.7% and 38% of total cell protein.

Example 6

Chromosomal expression of TGF-B2 using the double cassette binary system

A chromosomal transfer DNA encoding a fusion protein comprising DsbA, ubiquitin, and human TGF-β2 (DsbA::ubiquitin::TGF-β2) was created using the double cassette method. Construction of the fusion gene and chromosomal transfer DNA are shown in FIG. 21. DsbA::ubiquitin was from pDM25497, and TGF-β2 was PCR amplified from pPC-21 (Madisen et. al. (1988) DNA 7:1–8) using primers

UBTGFβ2F    5'-  GGG  GCC  GCG  GTG  GTG  CTT  TGG  ATG  CGG

CCT  ATT  GCT  TTA  GA-3' (SEQ ID NO:65)

and

TGFβ2R    5'-  GGG  GAA  TTC  TTA  GCT  GCA  TTT  GCA  AGA

CTT  TAC  A-3' (SEQ ID NO:66).

pDM25497 was digested with SacII-EcoRI and the 4.3 kb fragment containing pUC18 and DsbA::ubiquitin sequences was isolated. The 0.35 kb PCR product resulting from the amplification of pPC-21 encoding the last 112 amino acids of human TGF-β2 was purified and digested with SacII-EcoRI. These two fragments were ligated to create pDP26, a pUC18 derivative containing a DsbA::ubiquitin::TGF-β2 fusion gene. pDP26 was the donor construct for assembly of the binary plasmids used to make the chromosomal transfer DNA.

The fusion gene from pDP26 was ligated into the double-cassette binary vectors pDM25470 and pDM25465 to create pC9DP and pA6DP, respectively. Briefly, pDM 25470 was digested with BamHI-SmaI and the 4.2 kb fragment was isolated. pDP26 was digested with EcoRI, blunt ended with the Klenow fragment of DNA polymerase, and then digested with BamHI. The 1.1 kb fragment from this digest was isolated. The two fragments described above were ligated to create pC9DP.

pDM25465 was digested with BamHI, blunt ended with Klenow, digested with XbaI and the 7.1 kb fragment was isolated. pDP26 was digested with EcoRI, blunt ended with Klenow, digested with BamHI, and the 1.2 kb fragment was isolated. This 1.2 kb fragment was ligated to the 7.1 kb fragment from pDM25465 to create pA6DP.

An additional binary plasmid containing a tetracycline resistance selectable marker was created using the 7.2 kb fragment isolated from pDM46932 following XbaI-XhoI digestion, and the fusion gene from pA6DP (2.7 kb XbaI-XhoI fragment). These two fragments were ligated to create pA6DPIIT. EcoRI-XbaI fragments of pC9DP (2.2 kb) and pA6DPIIT (6.4 kb) were ligated to form the chromosomal transfer DNA (FIG. 21).

The chromosomal transfer DNA was transformed into *E. coli* strain B1384, which was grown in the presence of 500 μm IAA to induce the expression of INT and the integration of the chromosomal transfer DNA. Integrants were selected with 10 μg/ml kanamycin. All isolates were found to be ampicillin sensitive.

Isolates were further characterized by diagnostic PCR amplification of host cell chromosomal DNA. PCR amplifications with primer pairs 1227    5'-   TAA  TAC  GAC  TCA  CTA  TAG  GGA  GA-3' (SEQ ID NO:67)

β21079    5'-   GGA  AAT  GGA  TAC  ACG  AAC  CC-3' (SEQ ID NO:68), and

INT107    5'-   GCG  GAG  AAA  CCA  TAA  TTG  CAT  CTA

CTC-3' (SEQ ID NO:69)

-continued

6HEβ2    5'- GGG GGA TCC GAT CGT GGA GGA TGA TTA

AAT GCA CCA CCA CCA CCA CCA CGA CGA CGA CAA AGC

TTT GGA TGC GGC CTA T-3' (SEQ ID NO:70)

and primers T7REV and TRPBR2, described previously (see Example 2), confirmed the proper integration of the intact chromosomal transfer DNA into the chromosome at the att site.

Figure 26:
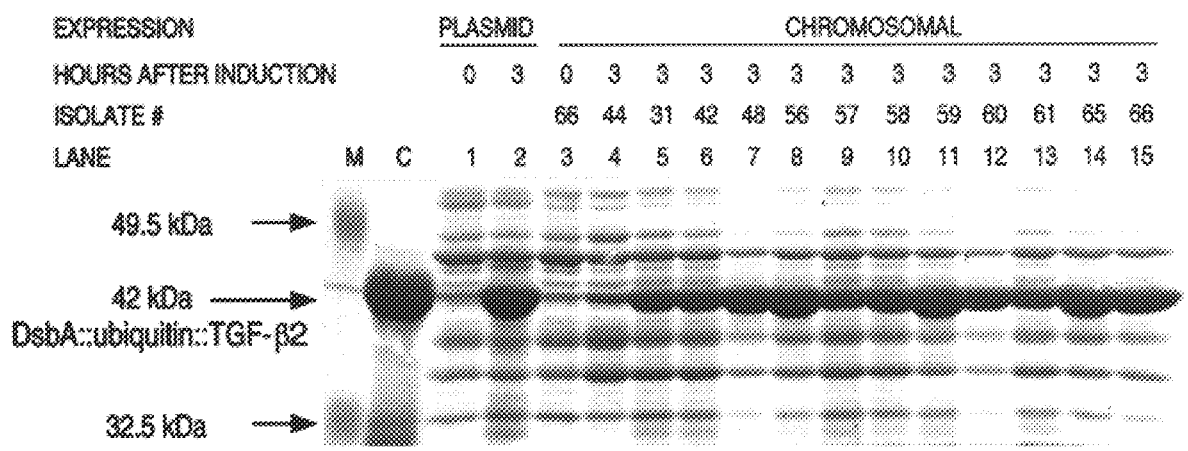
FIG. 26 shows a coomassie blue-stained SDS-PAGE gel showing protein accumulation from host cells expressing a gene encoding DsbA::ubiquitin::TGF-β2. M indicates molecular weight markers and C indicates a positive control. The two Plasmid lanes (Lanes 1 and 2) are used as a standard to compare protein accumulation from multicopy number plasmid vectors to protein accumulation from genes integrated into the chromosome. Lanes 3 and 4 are whole cell lysates of isolates which were negative for T7 RNA polymerase activity when streaked against phage 4107. Densitometric analysis of this gel showed that the plasmid strain accumulated protein to 26.4% of total cell protein. Protein accumulation was measured for isolates 48, 56, 59, 65 and 66, and showed protein accumulation to 36.7%, 33.3%, 32.1%, 29.5%, and 26.7%, respectively.

P1 lysates were prepared from a single isolate and used to transduce W3110DE3 to kanamycin resistance, as described previously. Amplification of the integrated fusion gene is accomplished by growth of kanamycin resistant isolates on medium containing kanamycin and tetracycline (30µg/ml). Kanamycin/tetracycline resistant isolates were assayed for T7 RNA polymerase activity by streaking against phage 4107, as described in Example 2. Isolates with T7 RNA polymerase activity were then tested for expression of the fusion gene by induction with IPTG, followed by analysis of protein expression by SDS-PAGE of whole cell lysates on 10% polyacrylamide gels (FIG. 26). Protein accumulation in chromosomal integrants was comparable to the levels seen in host cells containing a multicopy number plasmid utilizing the same T7 promoter linked to the a copy of the gene encoding the DsbA::ubiquitin::TGF-β2 fusion protein. Densitometric analysis showed that protein accumulation in chromosomal integrants was as high as 36.7% of total cell protein.

Example 7
Expression of a heterologous protein using a promoter-less CTD

This example shows the use of a chromosomal transfer DNA which does not carry a promoter. The chromosomal transfer DNA carries a segment of DNA homologous to a bacterial gene (in this example, lacZ or DsbA) linked in-frame to a DNA sequence encoding a heterologous protein of interest (in this case the DsbA::3C::IGF-I fusion protein of Example 5), as well as selectable marker genes. The homologous DNA encodes the 5' region of the bacterial gene. The chromosomal transfer DNA is introduced into the host cell, where it integrates into the homologous gene on the chromosome of the host cell, forming an operable linkage between the homologous gene's promoter and the DNA sequence encoding the heterologous protein of interest. Integrants are selected for using the selectable markers carried on the chromosomal transfer DNA. The heterologous protein of interest is expressed through the homologous gene's promoter (FIG. 8).

The DNA encoding the DsbA::3C::IGF-I fusion protein is constructed as described in Example 5. This fusion gene is then placed in frame to a DNA segment encoding the first 100 amino-terminal amino acids of the lacZ gene, forming a lacZ/DsbA::3C::IGF-I gene. The cyclophilin, kanamycin resistance, and tetracycline resistance genes utilized in Example 5 are also cloned into the plasmid carrying the lacZ/DsbA::3C::IGF-I gene. This plasmid is then cleaved with restriction endonucleases to remove the plasmid origin of replication, the ampicillin resistance gene and other non-essential sequences, then re-ligated to form a circular chromosomal transfer DNA. The chromosomal transfer DNA is transformed into E. coli host cells and the transformed host cells are grown on media containing kanamycin (10 µg/ml). Kanamycin resistant isolates are tested for ampicillin sensitivity, to show that the host cells carry integrated DNA, not plasmid DNA. Kan$^r$ isolates are also tested using PCR. PCR primers from the lacZ promoter and the DNA sequence encoding DsbA are used to confirm integration of the intact chromosomal transfer DNA. Amplification of the integrated fusion gene is selected for by growth of kan$^r$ isolates on medium containing kanamycin and tetracycline (30 µg/ml). Expression of the integrated fusion gene is induced by growth of kan$^r$/tet$^r$ isolates in the presence of IPTG. Protein expression is assayed by SDS-PAGE.

Promoter-less chromosomal transfer DNA's may also be integrated into other sites on the host cell chromosome (FIG. 9). Specialized host cells may be constructed which carry a chromosomal copy of an inducible promoter (in this case the T7 promoter) linked to a particular gene (in this case DsbA). This host cell is made by transforming a variant chromosomal transfer DNA (carrying a copy of the lacZ gene, the T7 promoter operably linked to the 5' end of the DsbA gene and the chloramphenicol resistance gene) into the host cell(in this case W3110DE3, which also carries a copy of the gene encoding T7 RNA polymerase). Integration of the chromosomal transfer DNA is selected for by growth of transformed W3110DE3 cells on medium containing chloramphenicol. The integration of the chromosomal transfer DNA produces a W3110DE3 host cell containing the T7 promoter linked to the 5' portion of the DsbA gene. This integrated DNA then becomes the target for integration of a chromosomal transfer DNA carrying a DNA sequence encoding the heterologous protein of interest.

A chromosomal transfer DNA carrying the DNA sequence encoding the heterologous protein of interest is constructed (in this case the DsbA::3C::IGF-I fusion gene described above and in Example 5). The cyclophilin, kanamycin resistance and tetracycline resistance genes are also cloned onto the plasmid. This plasmid is then cleaved with the appropriate restriction enzymes to remove the plasmid origin of replication, ampicillin resistance gene, and other non-essential sequences, and re-ligated to form a circular chromosomal transfer DNA. The chromosomal transfer DNA is transformed into the T7-DsbA W3110DE3 host cells described above. Integrants are selected by growth on medium containing chloramphenicol and kanamycin. Kan$^r$/cam$^r$ isolates are checked for integration of the intact chromosomal transfer DNA by PCR. PCR amplification of host cell chromosomal DNA using primer pairs T7F1× IGFREV confirms the integration of the intact chromosomal transfer DNA. Integrants are checked for T7 RNA polymerase activity by streaking against phage 4107, as described in Example 2. Amplification of the integrated DNA is selected for by growth of T7 RNA polymerase-positive isolates on kanamycin, chloramphenicol, and tetracycline. Resistant isolates are assayed for protein expression by induction with IPTG. Protein expression is assayed by SDS-PAGE.

Example 8
Expression of a DsbA::3C::IGFBP-3 fusion protein using the double cassette system A gene encoding DsbA::3C::IGFBP-3 fusion protein was expressed using the double cassette binary system shown in FIG. 7. The DsbA sequence was originally isolated by PCR amplification of the DsbA gene from the E. coli chromosome; plasmid pDM25454 was used as the source of the DsbA sequence for this fusion gene. The site for 3C protease was created by synthesizing two oligonucleotides,

RV3CTA 5'-CCCGATTCTCTGGAAGTTCTGTTCCAA-3' (SEQ ID NO:71)

and

Figure 22:
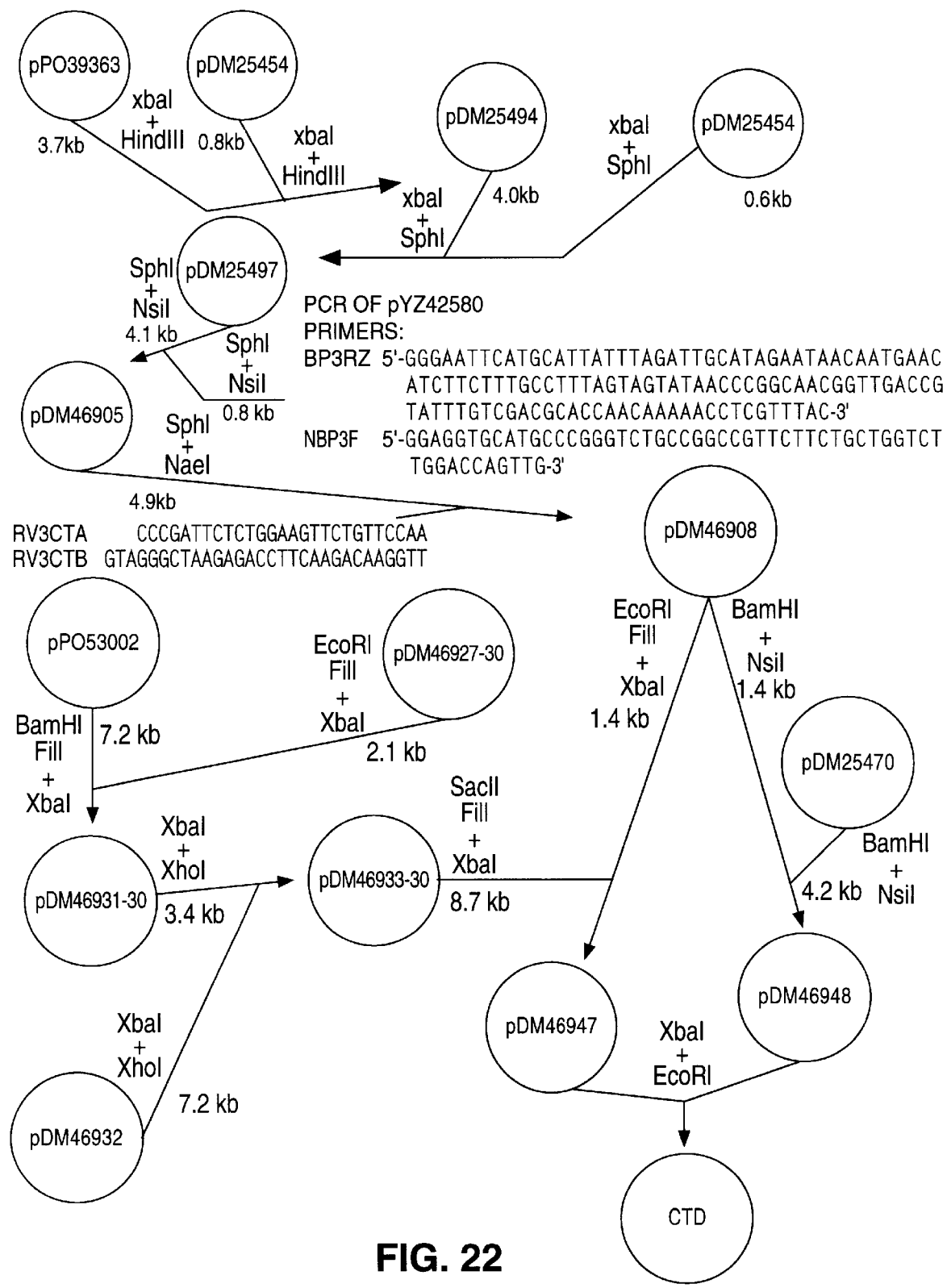
FIG. 22 (SEQ ID NO:76, SEQ ID NO:77, SEQ ID NO:80,and SEQ ID NO:81) shows the strategy used to construct the chromosomal transfer DNA used to integrate and express a gene encoding a DsbA::3C::IGFBP-3 fusion protein.
Figure 23:
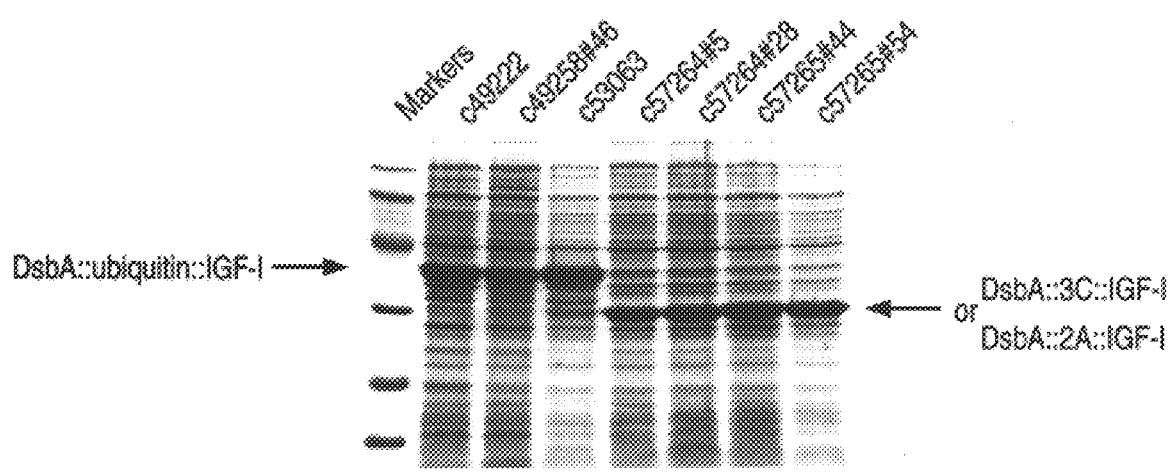
FIG. 23 shows an coomassie blue-stained SDS-PAGE gel of whole cell lysates of isolates expressing IGF-I fusion proteins. c49222, c49258#46, and c53063 express a DsbA::ubiquitin::IGF-I fusion protein (left arrow), which is easily visible. Surprising, this high level of expression is seen in c49222 and c49258#46, which were not amplified (i.e. there was no selection for chromosomal amplification of the integrated DNA). c57264#5 and c57264#28 express a DsbA::3C::IGF-I fusion protein while c57265#44 and c57265#54 express a DsbA::2A::IGF-I fusion protein. Again, the expressed fusion protein is easily visible. Densitometric analysis of this gel indicates that all of the isolates accumulate protein in excess 19% of total cell protein (average protein accumulation is 25.7% of total cell protein).

RV3CTB 5'-TTGGAACAGAACTTCCAGAGAATCGGGCATG-3' (SEQ ID NO:72), which were annealed to form a double stranded DNA fragment encoding a 3C protease cleavage site. The IGFBP-3 gene was constructed by annealing and ligating synthetic oligonucleotides, as described in Example 4. The IGFBP-3 sequence used for construction of the gene encoding the DsbA::3C::IGFBP-3 fusion protein was a PCR amplified DNA fragment made using primers BP3RZ and NBP3F and template pYZ42580. Cloning of the two DNA sources used to make chromosomal transfer DNA carrying the gene encoding the DsbA::3C::IGFBP-3 fusion protein, pDM46947 and pDM46948, is shown in FIG. 22.

The chromosomal transfer DNA was constructed using EcoRI/XbaI fragments from pDM46947 and pDM46948. The chromosomal transfer DNA was transformed into B1384 cells grown in the presence of indole acrylic acid (to induce the expression of INT). Integrants were selected for by growth of transformants on media containing kanamycin. All kanamycin resistant isolates were also ampicillin sensitive. Kanamycin resistant isolates were checked by PCR using primer pairs 1227×BP3–607, INT107×BP3–559, and T7REV×TRPBR2, as described in Example 4.

P1 lysates were prepared from one of the kanamycin resistant isolates and used to transduce W3110DE3 to kanamycin resistance. Kanamycin transductants were tested for the presence of T7 RNA polymerase activity by streaking against phage 4107, as described in Example 2. Kanamycin resistant/T7 RNA polymerase positive isolates were selected for chromosomal amplification by growth on media containing kanamycin and tetracycline. One $kan^r/tet^r$ isolate was selected and checked for protein expression by induction with IPTG. Protein accumulation was assayed by SDS-PAGE (FIG. 25 B). Densitometric analysis of an SDS-PAGE gel showed that the DsbA::3C::IGFBP-3 fusion protein accumulated to an average of 27.4% of total cell protein.

All publications, patents and patent applications cited in this specification are incorporated herein by reference to the same extent as if each individual publication, patent, or patent application was specifically and individually indicated to be incorporated by reference.

It should be apparent that one having ordinary skill in the art would be able to surmise equivalents to the claimed invention which would be within the spirit of the description above. Those equivalents are to be included within the scope of the present invention.

What is claimed is:

1. A method for producing a heterologous protein of interest, comprising the steps of:

transferring a chromosomal transfer DNA into a bacterial host cell, wherein said chromosomal transfer DNA comprises at least one copy of a gene encoding the heterologous protein of interest and a selectable marker, and wherein said host cell comprising a chromosome;

selecting for integration of said chromosomal transfer DNA into said host cell chromosome resulting in a host cell chromosome comprising a gene encoding a heterologous protein of interest operably linked to a promoter functional in the host cell and a selectable marker flanked by duplicate DNA; and expressing said gene, wherein said gene is at no time operably linked to a promoter functional in a host cell on a multicopy number plasmid vector during construction of the transfer DNA and wherein said heterologous protein of interest accumulates within said host cell to a level in excess of 0.1% of total cell protein.

2. The method of claim 1 wherein said chromosomal transfer DNA further comprises a promoter functional in said host cell, said promoter being operably linked to said gene encoding the heterologous protein of interest, and wherein the operable linkage is created by circularization of the chromosomal transfer DNA.

3. The method of claim 1 wherein said host cell chromosome further comprises a host cell promoter and said chromosomal transfer DNA further comprises a DNA sequence homologous to a segment of the host cell chromosome downstream from said host cell promoter, said DNA sequence linked in-frame to said gene encoding the heterologous protein of interest, wherein integration of said chromosomal transfer DNA results in the formation of an operable linkage between said DNA sequence and the host cell promoter.

4. The method of claim 1 wherein said heterologous protein of interest accumulates within said host cell to a level in excess of 1% of total cell protein.

5. The method of claim 1 wherein said heterologous protein of interest is a eukaryotic protein.

6. The method of claim 1 wherein said heterologous protein of interest is a mammalian protein.

7. The method of claim 1, wherein each said duplicate DNA comprises said gene encoding a heterologous protein of interest linked to said promoter.

8. The method of claim 1 further comprising selecting for chromosomal amplification of said chromosomal transfer DNA following integration of said chromosomal transfer DNA into the chromosome of said host cell.

9. A method for producing a chromosomal transfer DNA, comprising:

ligating a restriction fragment from each of a first plasmid vector and a second plasmid vector thereby producing a chromosomal transfer DNA, said first vector comprising a gene encoding a heterologous protein of interest lacking an operably linked promoter, said second vector comprising a promoter functional in a host cell, wherein said chromosomal transfer DNA comprises a selectable marker and lacks an origin of replication operable in said host cell.

10. A method for producing a chromosomal transfer DNA, comprising:

ligating a restriction fragment from each of a first plasmid vector and a second plasmid vector thereby producing a chromosomal transfer DNA, said first plasmid comprising a first gene encoding a heterologous protein of interest and a first promoter functional in a host cell, and wherein said first gene and first promoter are not operably linked, said second vector comprising a second gene encoding a heterologous protein of interest lacking an operably linked promoter, and a second promoter functional in a host cell, wherein said chromosomal transfer DNA comprises a selectable marker and lacks an origin of replication operable in said host cell and wherein said first gene is operably linked to said second promoter on the chromosomal transfer DNA and said second gene is operably linked to said first promoter on said chromosomal transfer DNA.

11. A chromosomal transfer DNA , comprising:

a gene encoding a heterologous protein of interest operably linked to a promoter functional in a host cell; and a selectable marker, said selectable marker flanked by duplicate DNA, wherein said gene encoding a heterologous protein of interest is at no time operably linked to a promoter functional in a host cell on a multicopy number plasmid vector.

12. A chromosomal transfer DNA, comprising:

two copies of a gene encoding a heterologous protein of interest, each of said copies being operably linked to a promoter functional in a host cell; and a selectable marker, said selectable marker flanked by said copies of said gene encoding a heterologous protein of interest, wherein each of said copies of said gene are at no time operably linked to a promoter functional in a host cell on a multicopy number plasmid vector.

* * * * *